(12) United States Patent
Fallin et al.

(10) Patent No.: US 11,241,225 B2
(45) Date of Patent: Feb. 8, 2022

(54) EXTRA JOINT STABILIZATION CONSTRUCT

(71) Applicant: Crossroads Extremity Systems, LLC, Memphis, TN (US)

(72) Inventors: T. Wade Fallin, Hyde Park, UT (US); Justin Taber, Honolulu, HI (US); Matthew Karam, North Liberty, IA (US); Phinit Phisitkul, Coralville, IA (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 269 days.

(21) Appl. No.: 16/545,371

(22) Filed: Aug. 20, 2019

(65) Prior Publication Data
US 2019/0380695 A1   Dec. 19, 2019

Related U.S. Application Data

(63) Continuation of application No. 15/641,592, filed on Jul. 5, 2017, now Pat. No. 10,426,459.
(Continued)

(51) Int. Cl.
*A61B 17/04* (2006.01)
*A61B 17/84* (2006.01)
(Continued)

(52) U.S. Cl.
CPC ...... *A61B 17/0401* (2013.01); *A61B 17/0485* (2013.01); *A61B 17/06166* (2013.01);
(Continued)

(58) Field of Classification Search
CPC combination set(s) only.
See application file for complete search history.

(56) References Cited

U.S. PATENT DOCUMENTS 2,181,746 A   11/1939   Siebrandt
2,291,413 A    7/1942   Siebrandt
(Continued)

FOREIGN PATENT DOCUMENTS

CA    551446 A    1/1958
EP    132284 A1   1/1985
(Continued)

OTHER PUBLICATIONS

European Search Report dated Jun. 29, 2021 for corresponding EP App. 17933290.3.
(Continued)

*Primary Examiner* — Sameh R Boles
(74) *Attorney, Agent, or Firm* — David Meibos; Maywood IP Law

(57) ABSTRACT

The disclosure provides devices and methods of use pertaining to extra joint stabilization. Embodiments include a number of suture returning and locking anchors that feature both a suture return element and a suture locking feature that employs an interference fit between a flexible synthetic strand, a receiver of the anchor, and a set screw, where the receiver and the set screw each have a number of gradual, opposing tapers to facilitate gradual proximal-to-distal gripping and releasing of the flexible strand to achieve an optimal locking force while preventing severing of the flexible strand. Embodiments also include a counter-torque anchor driver configured to resist torsional forces generated during and translated to the anchor during set-screw insertion. Further embodiments include extra joint reinforcement, stabilization, and attachment constructs formed using the disclosed devices. Other embodiments are disclosed.

20 Claims, 16 Drawing Sheets

Related U.S. Application Data

(60) Provisional application No. 62/358,231, filed on Jul. 5, 2016, provisional application No. 62/425,560, filed on Nov. 22, 2016, provisional application No. 62/456,217, filed on Feb. 8, 2017, provisional application No. 62/458,975, filed on Feb. 14, 2017.

(51) Int. Cl.
| | |
|---|---|
| *A61F 2/08* | (2006.01) |
| *A61B 17/06* | (2006.01) |
| *A61B 17/16* | (2006.01) |
| *A61B 90/00* | (2016.01) |
| *A61B 17/88* | (2006.01) |
| *A61B 17/80* | (2006.01) |
| *A61B 17/00* | (2006.01) |

(52) U.S. Cl.
CPC ........ *A61B 17/1604* (2013.01); *A61B 17/885* (2013.01); *A61B 17/8869* (2013.01); *A61B 90/06* (2016.02); *A61B 17/80* (2013.01); *A61B 17/848* (2013.01); *A61B 2017/00526* (2013.01); *A61B 2017/00867* (2013.01); *A61B 2017/0403* (2013.01); *A61B 2017/0404* (2013.01); *A61B 2017/044* (2013.01); *A61B 2017/045* (2013.01); *A61B 2017/0409* (2013.01); *A61B 2017/0414* (2013.01); *A61B 2017/0441* (2013.01); *A61B 2017/0445* (2013.01); *A61B 2017/0453* (2013.01); *A61B 2017/0464* (2013.01); *A61B 2090/061* (2016.02)

(56) References Cited

U.S. PATENT DOCUMENTS

| | | |
|---|---|---|
| 2,362,957 A | 11/1944 | Hackett |
| 2,427,128 A | 9/1947 | Ettinger |
| 2,485,531 A | 10/1949 | William |
| 2,489,870 A | 11/1949 | William |
| 2,511,051 A | 6/1950 | William |
| 2,706,475 A | 4/1955 | Reynolds |
| 2,715,403 A | 8/1955 | Jordan |
| 3,114,367 A | 12/1963 | Carpenter |
| 3,664,022 A | 5/1972 | Small |
| 3,727,611 A | 4/1973 | Schultz |
| 3,867,932 A | 2/1975 | Huene |
| 3,959,960 A | 6/1976 | Santos |
| 4,050,464 A | 9/1977 | Hall |
| 4,159,716 A | 7/1979 | Borchers |
| 4,364,381 A | 12/1982 | Sher |
| D273,326 S | 4/1984 | Peterson |
| 4,586,497 A | 5/1986 | Dapra |
| 4,587,963 A | 5/1986 | Leibinger |
| 4,712,542 A | 12/1987 | Daniel |
| 4,787,377 A | 11/1988 | Laboureau |
| 4,945,904 A | 8/1990 | Bolton |
| 4,964,862 A | 10/1990 | Arms |
| 4,969,471 A | 11/1990 | Daniel |
| 4,969,895 A | 11/1990 | McLeod |
| 5,035,701 A | 7/1991 | Kabbara |
| 5,116,340 A | 5/1992 | Songer |
| 5,300,077 A | 4/1994 | Howell |
| 5,306,290 A | 4/1994 | Martins |
| 5,312,410 A | 5/1994 | Miller |
| 5,312,412 A | 5/1994 | Whipple |
| 5,409,490 A | 4/1995 | Ethridge |
| 5,431,659 A | 7/1995 | Ross, Jr |
| 5,449,361 A | 9/1995 | Preissman |
| 5,476,465 A | 12/1995 | Preissman |
| 5,540,698 A | 7/1996 | Preissman |
| 5,545,168 A | 8/1996 | Burke |
| 5,570,706 A | 11/1996 | Howell |
| 5,578,057 A | 11/1996 | Wenstrom, Jr. |
| 5,584,839 A | 12/1996 | Gieringer |
| 5,643,321 A | 1/1997 | McDevitt |
| 5,702,397 A | 12/1997 | Goble et al. |
| 5,713,897 A | 2/1998 | Goble |
| 5,725,532 A | 3/1998 | Shoemaker |
| 5,741,281 A | 4/1998 | Martin |
| 5,868,748 A | 2/1999 | Burke |
| 5,895,389 A | 4/1999 | Schenk |
| 6,001,106 A | 12/1999 | Ryan |
| 6,027,523 A | 2/2000 | Schmieding |
| 6,045,573 A | 4/2000 | Wenstrom |
| 6,254,604 B1 | 7/2001 | Howell |
| 6,254,605 B1 | 7/2001 | Howell |
| 6,368,326 B1 | 4/2002 | Dakin |
| 6,443,955 B1 | 9/2002 | Ahrend |
| 6,478,753 B2 | 11/2002 | Reay |
| 6,482,208 B1 | 11/2002 | Ahrend |
| 6,517,564 B1 | 2/2003 | Grafton |
| 6,527,794 B1 | 3/2003 | McDevitt |
| 6,547,778 B1 | 4/2003 | Sklar |
| 6,554,852 B1 | 4/2003 | Oberlander |
| 6,557,426 B2 | 5/2003 | Reinemann, Jr |
| 6,616,667 B1 | 9/2003 | Steiger |
| 6,660,023 B2 | 12/2003 | McDevitt |
| 6,669,698 B1 | 12/2003 | Tromanhauser |
| 6,739,068 B1 | 5/2004 | Rinner |
| 6,761,722 B2 | 7/2004 | Cole |
| 6,780,198 B1 | 8/2004 | Gregoire |
| 6,866,673 B2 | 3/2005 | Oren |
| 7,060,068 B2 | 6/2006 | Tromanhauser |
| 7,081,126 B2 | 7/2006 | McDevitt |
| 7,083,638 B2 | 8/2006 | Foerster |
| 7,090,690 B2 | 8/2006 | Foerster |
| 7,160,285 B2 | 1/2007 | Sklar |
| 7,172,626 B1 | 2/2007 | Andrews |
| 7,211,088 B2 | 5/2007 | Grafton |
| 7,226,469 B2 | 6/2007 | Benavitz |
| 7,235,091 B2 | 6/2007 | Thornes |
| 7,326,222 B2 | 2/2008 | Dreyfuss |
| 7,431,692 B2 | 10/2008 | Zollinger |
| 7,442,202 B2 | 10/2008 | Dreyfuss |
| 7,455,683 B2 | 11/2008 | Geissler |
| 7,537,596 B2 | 5/2009 | Jensen |
| 7,556,630 B2 | 7/2009 | Molz |
| 7,572,275 B2 | 8/2009 | Fallin |
| 7,578,824 B2 | 8/2009 | Justin |
| 7,637,926 B2 | 12/2009 | Foerster |
| 7,871,368 B2 | 1/2011 | Zollinger |
| 7,875,058 B2 | 1/2011 | Holmes, Jr. |
| 7,887,551 B2 | 2/2011 | Bojarski |
| 7,901,431 B2 | 3/2011 | Shumas |
| 7,963,966 B2 | 6/2011 | Cole |
| 7,998,149 B2 | 8/2011 | Hamilton |
| 8,083,769 B2 | 12/2011 | Cauldwell |
| 8,109,936 B2 | 2/2012 | Tipirneni |
| 8,114,127 B2 | 2/2012 | West |
| 8,114,128 B2 | 2/2012 | Cauldwell |
| 8,162,997 B2 | 4/2012 | Struhl |
| 8,167,906 B2 | 5/2012 | Cauldwell |
| 8,182,495 B2 | 5/2012 | DiStefano |
| 8,221,455 B2 | 7/2012 | Shumas |
| 8,277,459 B2 | 10/2012 | Sand |
| 8,277,484 B2 | 10/2012 | Barbieri |
| 8,298,247 B2 | 10/2012 | Sterrett |
| 8,303,591 B1 | 11/2012 | Foerster |
| 8,317,828 B2 | 11/2012 | Martinek |
| 8,343,186 B2 | 1/2013 | Dreyfuss |
| 8,394,123 B2 | 3/2013 | Cauldwell |
| 8,414,599 B1 | 4/2013 | Foerster |
| 8,460,379 B2 | 6/2013 | Albertorio |
| 8,500,745 B2 | 8/2013 | Kuenzi |
| 8,506,597 B2 | 8/2013 | Kaiser |
| 8,579,901 B1 | 11/2013 | Foerster |
| 8,597,328 B2 | 12/2013 | Cauldwell |
| 8,613,755 B1 | 12/2013 | Foerster |
| 8,617,185 B2 | 12/2013 | Bonutti |
| 8,623,049 B2 | 1/2014 | Ward |
| 8,623,051 B2 | 1/2014 | Bojarski |
| 8,623,052 B2 | 1/2014 | Dreyfuss |

(56) References Cited

U.S. PATENT DOCUMENTS

| | | |
|---|---|---|
| 8,679,122 B2 | 3/2014 | Bernstein |
| 8,696,719 B2 | 4/2014 | Lofthouse |
| 8,715,297 B1 | 5/2014 | Foerster |
| 8,764,763 B2 | 7/2014 | Foerster |
| 8,764,797 B2 | 7/2014 | Dreyfuss |
| 8,790,344 B1 | 7/2014 | Foerster |
| 8,795,286 B2 | 8/2014 | Sand |
| 8,801,755 B2 | 8/2014 | Dreyfuss |
| 8,814,902 B2 | 8/2014 | Bonutti |
| 8,821,541 B2 | 9/2014 | Dreyfuss |
| 8,870,876 B2 | 10/2014 | Lettmann |
| 8,876,900 B2 | 11/2014 | Guederian |
| 8,882,833 B2 | 11/2014 | Saylor |
| 8,888,815 B2 | 11/2014 | Holmes, Jr. |
| 8,926,626 B2 | 1/2015 | Mannava |
| 8,939,999 B2 | 1/2015 | Sterrett |
| 8,945,026 B2 | 2/2015 | Moser |
| 8,961,575 B2 | 2/2015 | Choinski |
| 8,979,850 B2 | 3/2015 | Johnstone |
| 8,984,720 B2 | 3/2015 | Gephart |
| 9,017,330 B2 | 4/2015 | Foerster |
| 9,039,682 B2 | 5/2015 | Lampropoulos et al. |
| 9,072,509 B2 | 7/2015 | Stoll, Jr |
| 9,107,701 B2 | 8/2015 | Cole |
| 9,131,937 B2 | 9/2015 | Chan |
| 9,138,219 B2 | 9/2015 | Horrell |
| 9,161,748 B2 | 10/2015 | West |
| 9,179,907 B2 | 11/2015 | ElAttrache |
| 9,179,950 B2 | 11/2015 | Zajac |
| 9,186,133 B2 | 11/2015 | Gregoire |
| 9,204,872 B2 | 12/2015 | Loepke |
| 9,259,217 B2 | 2/2016 | Fritzinger |
| 9,271,715 B2 | 3/2016 | Cauldwell |
| 9,277,912 B2 | 3/2016 | Donate |
| 9,521,999 B2 | 12/2016 | Dreyfuss |
| 9,526,493 B2 | 12/2016 | Dreyfuss |
| 9,532,776 B2 | 1/2017 | Lo |
| 9,549,726 B2 | 1/2017 | Dreyfuss |
| 9,622,739 B2 | 4/2017 | Dreyfuss |
| 2001/0049483 A1 | 12/2001 | Reay |
| 2002/0087190 A1 | 7/2002 | Benavitz |
| 2002/0188297 A1 | 12/2002 | Dakin |
| 2003/0009171 A1 | 1/2003 | Tornier |
| 2003/0176920 A1 | 9/2003 | Sklar |
| 2004/0098045 A1 | 5/2004 | Grafton |
| 2004/0102788 A1 | 5/2004 | Huebner |
| 2004/0153153 A1 | 8/2004 | Elson |
| 2005/0065533 A1 | 3/2005 | Magen |
| 2005/0070906 A1 | 3/2005 | Clark |
| 2005/0222618 A1 | 10/2005 | Dreyfuss |
| 2005/0240226 A1 | 10/2005 | Foerster |
| 2006/0085006 A1 | 4/2006 | Ek |
| 2006/0161159 A1 | 7/2006 | Dreyfuss |
| 2006/0271060 A1 | 11/2006 | Gordon |
| 2006/0276804 A1 | 12/2006 | Molz |
| 2006/0293709 A1 | 12/2006 | Bojarski |
| 2007/0060922 A1 | 3/2007 | Dreyfuss |
| 2007/0060931 A1 | 3/2007 | Hamilton |
| 2007/0073299 A1 | 3/2007 | Dreyfuss |
| 2007/0083236 A1 | 4/2007 | Sikora |
| 2007/0088362 A1 | 4/2007 | Bonutti |
| 2007/0150003 A1 | 6/2007 | Dreyfuss |
| 2007/0198036 A1 | 8/2007 | Sklar |
| 2007/0225764 A1 | 9/2007 | Benavitz |
| 2007/0288027 A1 | 12/2007 | Grafton |
| 2008/0077182 A1 | 3/2008 | Geissler |
| 2008/0249567 A1 | 10/2008 | Kaplan |
| 2009/0043153 A1 | 2/2009 | Zollinger |
| 2009/0157124 A1 | 6/2009 | Ferragamo et al. |
| 2009/0228049 A1 | 9/2009 | Park |
| 2009/0306711 A1 | 12/2009 | Stone et al. |
| 2010/0010496 A1 | 1/2010 | Isaza |
| 2010/0160963 A1 | 6/2010 | Fallin |
| 2010/0191284 A1 | 7/2010 | Dreyfuss |
| 2010/0262185 A1* | 10/2010 | Gelfand ............ A61B 17/0401 606/232 |
| 2011/0022054 A1 | 1/2011 | DiStefano |
| 2011/0112576 A1 | 5/2011 | Nguyen |
| 2011/0184426 A1 | 7/2011 | Garces Martin |
| 2011/0224727 A1 | 9/2011 | Housman |
| 2012/0053626 A1 | 3/2012 | Koepke |
| 2012/0060847 A1 | 3/2012 | Stratton |
| 2012/0065677 A1 | 3/2012 | West |
| 2012/0123417 A1 | 5/2012 | Smith |
| 2012/0123428 A1 | 5/2012 | Berberich |
| 2012/0165867 A1 | 6/2012 | Denham et al. |
| 2012/0172936 A1 | 7/2012 | Horrell |
| 2012/0253410 A1 | 10/2012 | Taylor |
| 2013/0023930 A1 | 1/2013 | Stone et al. |
| 2013/0138150 A1 | 5/2013 | Baker |
| 2013/0165972 A1 | 6/2013 | Sullivan |
| 2013/0184708 A1 | 7/2013 | Robinson |
| 2013/0296937 A1 | 11/2013 | Dreyfuss |
| 2013/0345750 A1 | 12/2013 | Sullivan |
| 2014/0018828 A1 | 1/2014 | Foerster |
| 2014/0031882 A1 | 1/2014 | Schmuck |
| 2014/0039551 A1 | 2/2014 | Donahue |
| 2014/0074163 A1 | 3/2014 | West |
| 2014/0081322 A1 | 3/2014 | Sengun |
| 2014/0081323 A1 | 3/2014 | Hawkins |
| 2014/0081324 A1 | 3/2014 | Sengun |
| 2014/0081325 A1 | 3/2014 | Sengun |
| 2014/0114353 A1 | 4/2014 | Bojarski |
| 2014/0121701 A1 | 5/2014 | Dreyfuss |
| 2014/0128915 A1 | 5/2014 | Dreyfuss |
| 2014/0194907 A1 | 7/2014 | Bonutti |
| 2014/0194927 A1 | 7/2014 | Kaiser |
| 2014/0277128 A1 | 9/2014 | Moore et al. |
| 2014/0277134 A1 | 9/2014 | ElAttrache |
| 2014/0364905 A1 | 12/2014 | Lunn |
| 2014/0364909 A1 | 12/2014 | Dreyfuss |
| 2014/0371749 A1 | 12/2014 | Foerster |
| 2014/0379028 A1 | 12/2014 | Lo |
| 2015/0005779 A1 | 1/2015 | Tepic |
| 2015/0005819 A1 | 1/2015 | Dreyfuss |
| 2015/0012015 A1 | 1/2015 | Berelsman |
| 2015/0039029 A1 | 2/2015 | Wade |
| 2015/0051601 A1 | 2/2015 | Larsen |
| 2015/0073475 A1 | 3/2015 | Schaller |
| 2015/0073477 A1 | 3/2015 | Holmes, Jr. |
| 2015/0173739 A1 | 6/2015 | Rodriguez et al. |
| 2015/0201923 A1 | 7/2015 | Fan |
| 2015/0216576 A1 | 8/2015 | Foerster |
| 2015/0272567 A1 | 10/2015 | Feezor |
| 2015/0289868 A1 | 10/2015 | Sauer |
| 2015/0305737 A1 | 10/2015 | Conley |
| 2015/0313640 A1 | 11/2015 | O'Daly |
| 2015/0342594 A1 | 12/2015 | Stone |
| 2015/0342596 A1 | 12/2015 | Dreyfuss |
| 2015/0342651 A1 | 12/2015 | Cole |
| 2015/0351741 A1 | 12/2015 | Hawkins |
| 2015/0351809 A1 | 12/2015 | Jackson et al. |
| 2016/0008041 A1 | 1/2016 | Makhlouf |
| 2016/0022320 A1 | 1/2016 | Jackson et al. |
| 2016/0038186 A1 | 2/2016 | Herzog et al. |
| 2016/0038201 A1 | 2/2016 | Cummings |
| 2016/0038267 A1 | 2/2016 | Allen |
| 2016/0051250 A1 | 2/2016 | Thornes |
| 2016/0051251 A1 | 2/2016 | Koepke |
| 2016/0066901 A1 | 3/2016 | Gregoire |
| 2016/0089131 A1 | 3/2016 | Wade |
| 2016/0192924 A1 | 7/2016 | Cauldwell |
| 2016/0235399 A1 | 8/2016 | Housman |
| 2016/0270902 A1 | 9/2016 | Snedeker et al. |
| 2016/0287302 A1 | 10/2016 | Horrell |
| 2016/0374661 A1 | 12/2016 | Housman et al. |
| 2017/0071592 A1 | 3/2017 | Feezor et al. |

FOREIGN PATENT DOCUMENTS

| | | |
|---|---|---|
| ES | 2226791 T3 | 4/2005 |
| JP | 2002102236 A | 4/2002 |
| WO | WO2006130179 | 12/2006 |

(56) References Cited

FOREIGN PATENT DOCUMENTS

| WO | 2007102829 A1 | 9/2007 |
|---|---|---|
| WO | WO2009055800 | 4/2009 |
| WO | 2011153417 A1 | 12/2011 |
| WO | 2012092027 A2 | 7/2012 |

OTHER PUBLICATIONS

European Search Report dated Jul. 22, 2021 for corresponding EP App. 17933461.0.
Akros Fibulink, Akros Medical, 2017, www.akrosmedical.com, 3 pp.
Deltoid Ligament Reconstruction Tunnel Sites, Arthrex, Inc., www.arthrex.com, 2014, 2 pp.
InternalBrace—Ligament Augmentaion Repair—Deltoid Ligament, Arthex, Inc., www.arthrex.com, 2015, 2 pp.
InternalBrace—Advanced Treatment for Ligament & Tendon Repair, Arthrex, Inc., www.arthrex.com, 2 pp.
InternalBrace—Ligament Augmentation Repair, Arthrex, Inc., www.arthrex.com, 2015, 2 pp.
Modified Brostrom-Gould Technique for Lateral Ankle Ligament Reconstruction—Surgical Technique, Arthrex, Inc., www.arthrex.com, 2015, 6 pp.
Knotless TightRope Syndesmosis Fixation—Surgical Technique, Arthrex, Inc., www.arthrex.com, 2015, 5 pp.
Get your athlete back in the game!—Syndesmosis TightRope, Arthrex, Inc., http://cptr.it/TRHAS, 2015, 1 pp.
ZipTight Fixation System, BioMet Sports Medicine, www.biometsportsmedicine.com, 2009, 8 pp.
Nelson, Owen A., "Examination and Repair of the AITFL in Transmalleolar Fractures", J. Orthop Trauma, vol. 20, No. 9, Oct. 2006, p. 637-643.
INVISIKNOT—Foot and Ankle Technique Guide—Ankle Syndesmosis Repair, Operative Technique, Smith & Nephew, Inc., www.smith-nephew.com, Jun. 2017, 8 pp.
INVISIKNOT—Ankle Syndesmosis Repair Kit, Smith & Nephew, Inc., www.smith-nephew.com, 1 pp.
Van Heest, Tyler J., et al., "Injuries to the Ankle Syndesmosis", J. Bone Joint Surg. Am. 2014;96:603-13, http://dx.dor.org/10.2106/JBJS.M.00094, 11 pp.
International Search Report and Written Opinion for Int. Appl. No. PCT/US2017/064173 dated Feb. 14, 2018, 8 pp.
International Search Report and Written Opinion for Int. Appl. No. PCT/US2017/064178 dated Sep. 3, 2018, 9 pp.

* cited by examiner

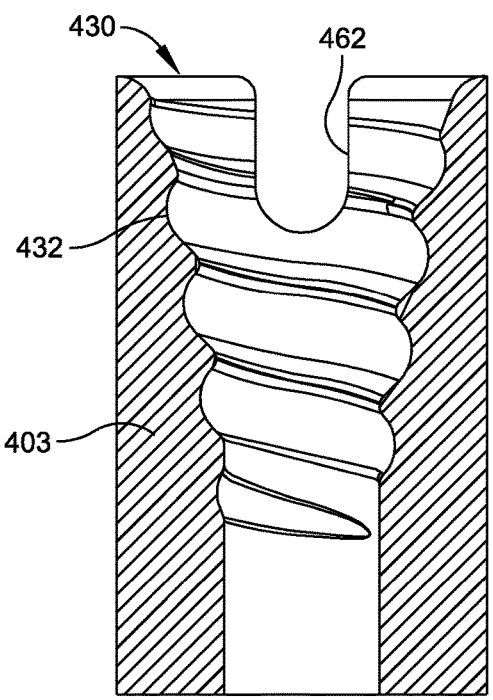
FIG. 8
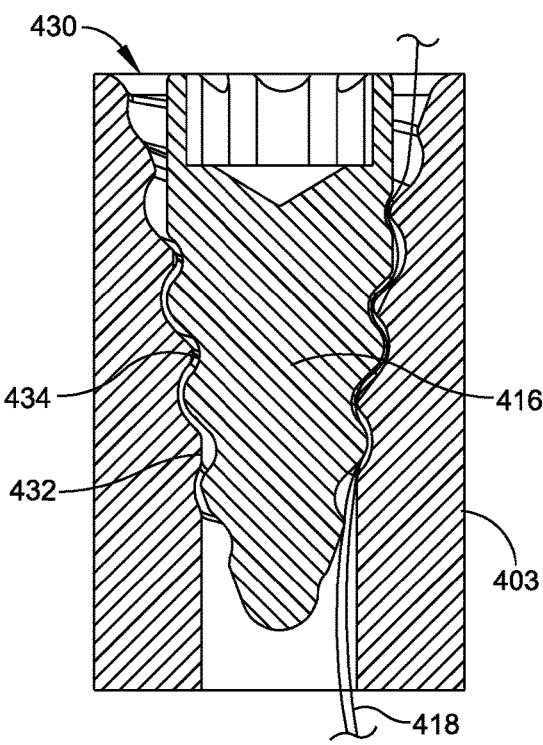
FIG. 9
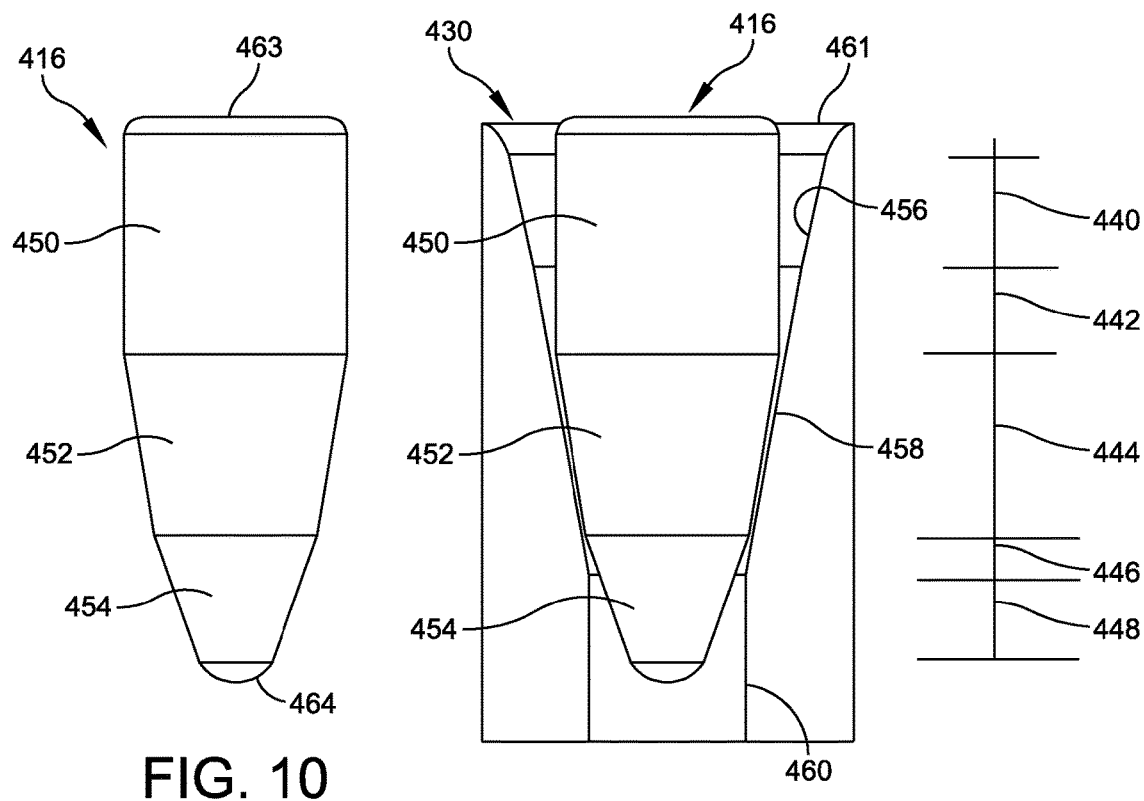
FIG. 10
FIG. 11

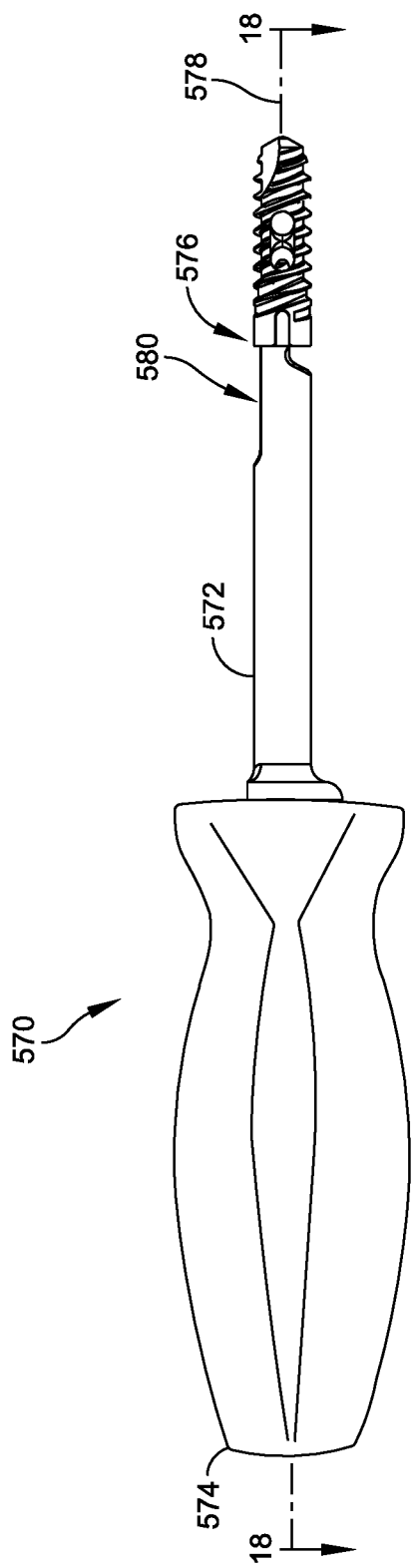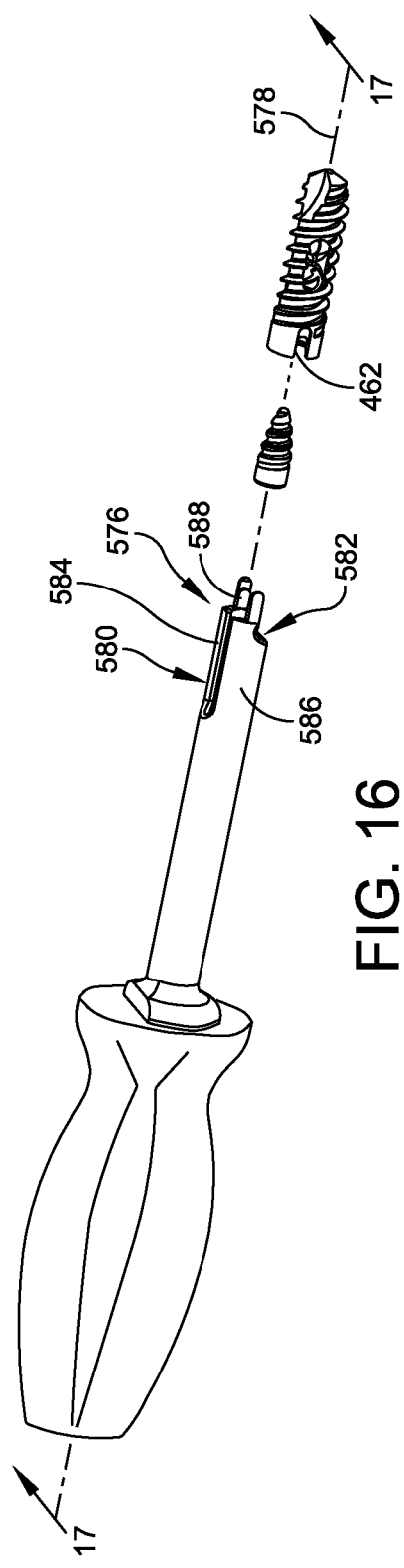

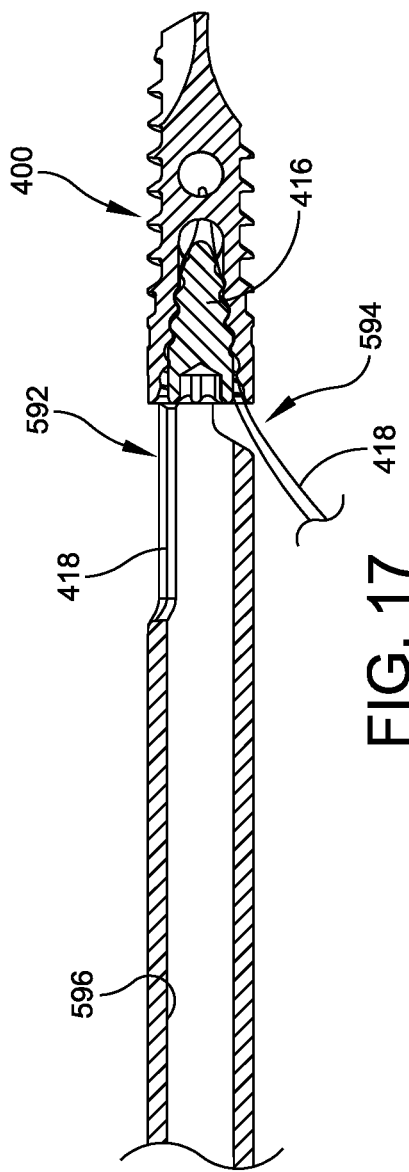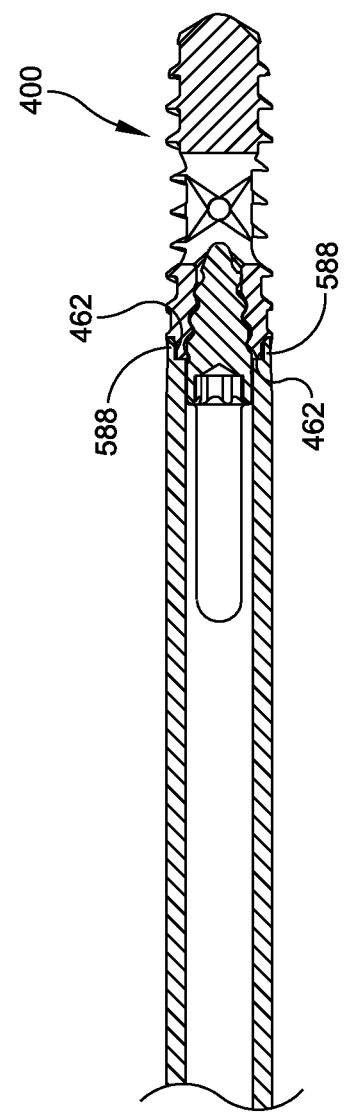

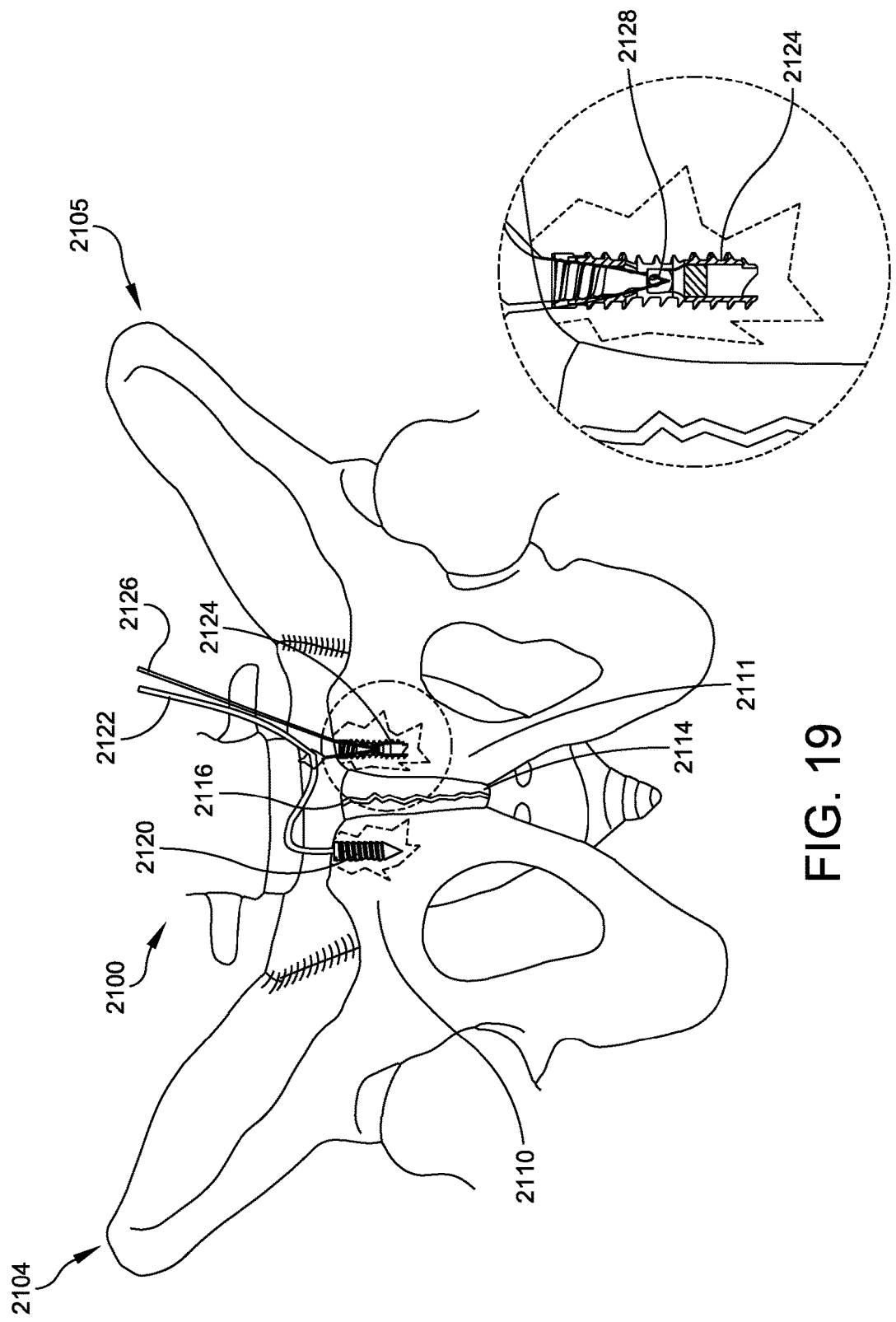

US 11,241,225 B2

EXTRA JOINT STABILIZATION CONSTRUCT

REFERENCE TO PENDING PRIOR PATENT APPLICATIONS

This application claims the benefit under 35 U.S.C. 119(e) of U.S. Provisional Patent Application Nos. 62/358,231, filed Jul. 5, 2016 by Justin Taber and T. Wade Fallin for "LIGAMENT REINFORCEMENT DEVICES AND METHODS," 62/425,560 filed Nov. 22, 2016 by Justin Tabor, Phinit Phisitkul, and T. Wade Fallin for "LIGAMENT REINFORCEMENT DEVICES AND METHODS," 62/456,217, filed Feb. 8, 2017 by Justin Taber and T. Wade Fallin for "PLATE AND LOOP CONSTRUCT," and 62/458,975, filed Feb. 14, 2017 by Matthew Karam, Phinit Phisitkul, Justin Taber, and T. Wade Fallin for "PELVIC FRACTURE REPAIR," all of which patent applications are hereby incorporated herein by reference.

REFERENCE TO CO-FILED APPLICATIONS

This application was co-filed with the following U.S. Patent Application Numbers on Jul. 5, 2017: Ser. No. 15/641,573 by Matthew Karam, Phinit Phisitkul, Justin Taber and T. Wade Fallin for "INTRA JOINT STABILIZATION CONSTRUCT," Ser. No. 15/641,600 by Justin Taber and T. Wade Fallin for "NONCIRCULAR BROACH AND METHODS OF USE," Ser. No. 15/641,618 by Phinit Phisitkul, Justin Taber, and T. Wade Fallin for "MULTIPLE SUTURE THREADER AND METHOD OF USE," and Ser. No. 15/642,053 by Justin Taber and T. Wade Fallin for "COMPRESSION AND TENSION INSTRUMENTS AND METHODS OF USE TO REINFORCE LIGAMENTS," all of which patent applications are incorporated herein by reference.

BACKGROUND

Ligaments interconnect bones of the skeletal system and are involved with the stabilization and kinematics of skeletal joints. Various injuries may occur that result in compromised ligament function and/or bone fractures. Such injuries include, for example, partial and complete tears and avulsion of the bone where a ligament attaches to a bone. Such injuries occur throughout the skeletal system.

By way of example, the human pelvis 2100 is a complex junction of multiple bones and soft tissues, as shown in FIG. 1. The sacrum 2102 bounds the posterior aspect of the pelvis with a pair of hip bones 2104, 2105 bounding the lateral and anterior aspects of the pelvis. Each hip bone is composed of three parts including the ilium 2106, 2107; ischium 2108, 2109; and pubis 2110, 2111. The sacrum is joined to each hip bone 2104, 2105 by strong ligaments at the sacroiliac joint 2112, 2113. The hip bones 2104, 2105 are joined anteriorly at the cartilaginous pubic symphysis 2114.

Various conditions may cause the pelvis to become unstable. For example, childbirth and traumatic injury may result in instability at the sacroiliac joint 2112, 2113 and/or the pubic symphysis 2114. For example, a traumatic anterior-posterior compression fracture may result in a separation 2116 between the hip bones at the pubic symphysis 2114, as shown in FIG. 1, and loosening of the sacroiliac joint 2112, 2113 leading to pelvic instability.

In another example, the human ankle 100 is a complex junction of multiple bones and soft tissues, as shown in FIGS. 2-4. The ankle includes joints between the tibia 102, fibula 104, and talus 106. The joint between the tibia 102 and fibula 104 is a syndesmosis or slightly movable joint in which the bones are joined together by connective tissue. The syndesmosis between the tibia and fibula includes the anterior inferior tibiofibular ligament (AITFL) 110, the posterior inferior tibiofibular ligament (PITFL) 112, and the interosseous ligament (IOL) 114 (FIG. 4). The syndesmosis ligaments are often injured in high ankle sprains. Other injury prone ligaments of the ankle joint include, among others, the anterior talofibular ligament (ATFL) 120, the posterior talofibular ligament (PTFL) 122 and the deltoid ligament complex 124 including superficial and deep deltoid ligaments.

What is needed is improved implants, instruments and methods to stabilize bone fractures and/or reinforce ligaments.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a knotless returning and locking system for bone fracture stabilization and soft tissue repair and reinforcement. The system comprises a returning and locking anchor having a body with a proximal end, a distal end, and defining a longitudinal axis, the body forming an internal passage and a return feature, the internal passage having a threaded receiver located at the proximal end of the body and including a proximal portion, a mid portion, and a distal portion, the return feature located distal to the threaded receiver and in communication with the internal passage. The system also includes a threaded set screw having a proximal portion, a mid portion, and a distal portion, the threaded set screw configured for rotational insertion into the threaded receiver to achieve a progressively increasing interference fit about a flexible synthetic strand passing between the proximal portions and the mid portions of the threaded receiver and the threaded set screw and a progressively decreasing interference fit about the flexible synthetic strand passing between the mid portions and the distal portions of the threaded receiver and the threaded set screw. The progressively increasing interference fit and the progressively decreasing interference fit combine to provide a locking feature that reversibly secures the flexible synthetic strand in relation to the returning and locking anchor.

Another embodiment provides a counter-torque driver for rotationally driving an anchor into bone, the anchor having a proximal end, a distal end, and a driver feature, the driver feature comprising two opposing slots formed in the proximal end of the anchor. The counter-torque driver comprises a longitudinal body extending from a proximal end to a distal end and defining a longitudinal axis, the longitudinal body including an axial through hole extending from the proximal end to the distal end along the longitudinal axis. The counter-torque driver also includes two opposing tabs extending from the distal end of the body, the two tabs centered about the longitudinal axis and configured to engage with the two opposing slots formed in the proximal end of the anchor. When the two opposing tabs of the driver are engaged with the two opposing slots of the anchor and the driver is rotated, the suture anchor is rotationally driven into the bone. When the two opposing tabs of the driver are engaged with the two opposing slots of the anchor and the driver is held stationary, each of the tabs provides a distal facing bearing surface to resist torsional forces generated when tensioning a flexible synthetic strand via a rotational input to a set screw inserted through the axial through hole of the driver into the anchor, thereby countering the torsional forces to maintain an original insertion alignment of the anchor within the bone.

Yet another embodiment provides an external construct for stabilizing a joint. The construct comprises a flexible synthetic strand having first and second opposing ends, a first fixation secured at the first end of the flexible synthetic strand, and a second fixation secured at the second end of the flexible synthetic strand. The second fixation comprises a returning and locking anchor inserted into a bone portion, where the returning and locking anchor has a body with a proximal end, a distal end, and defines a longitudinal axis, and where the body forms an internal passage having a threaded receiver located at the proximal end and a return feature located distal to the threaded receiver and in communication with the internal passage, where (1) the second end of the flexible synthetic strand enters the returning and locking anchor through the axial passage at the proximal end of the body, routes around the return feature, and exits the returning and locking anchor through the axial passage at the proximal end of the body; (2) the flexible synthetic strand is tensioned between the first and the second fixations; and (3) the second end of the flexible synthetic strand is locked relative to the returning and locking anchor via a threaded set screw that is rotationally inserted into the threaded receiver resulting in a continuous, uninterrupted length of the flexible synthetic strand extending externally across the joint between the first and the second fixations.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which:

FIG. 8 illustrates a cross-sectional view of a receiver of a suture locking feature of the suture returning and locking anchor of FIGS. 5-7;

FIG. 9 illustrates a cross-sectional view of the receiver of FIG. 8 having a set screw inserted therein to form an interference fit between a suture and the receiver and the set screw;

FIG. 10 illustrates a front view of the set screw of FIG. 9 without threading;

FIG. 11 illustrates the cross-sectional view of the set screw and the receiver of FIG. 9, without threading;

FIGS. 15-18 illustrate respective side, perspective-exploded, and cross-sectional views of one embodiment of an anchor driver engaging with the returning and locking anchor of FIGS. 5-7;

FIGS. 19-22 show partial sectional anterior views of the pelvis of FIG. 1 and illustrate the steps of an operative sequence for stabilizing the compression fracture of FIG. 1 using embodiments of the disclosed devices;

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

The technology discussed herein relates to apparatus and corresponding methods of use for preparing ligament reinforcement and bone fracture repair constructs. Embodiments include a number of suture returning and locking anchors, anchor drivers, and extra joint ligament reinforcement and/or bone fracture repair constructs constructed via operative methods employing the devices and instruments described herein.

Combined Suture Returning and Locking Anchors

Figure 5:
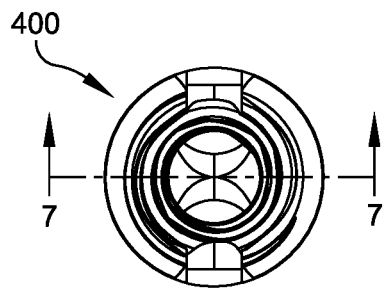
FIGS. 5-7 illustrate respective top, front, and cross-sectional views of one embodiment of a returning and locking anchor.
Figure 6:
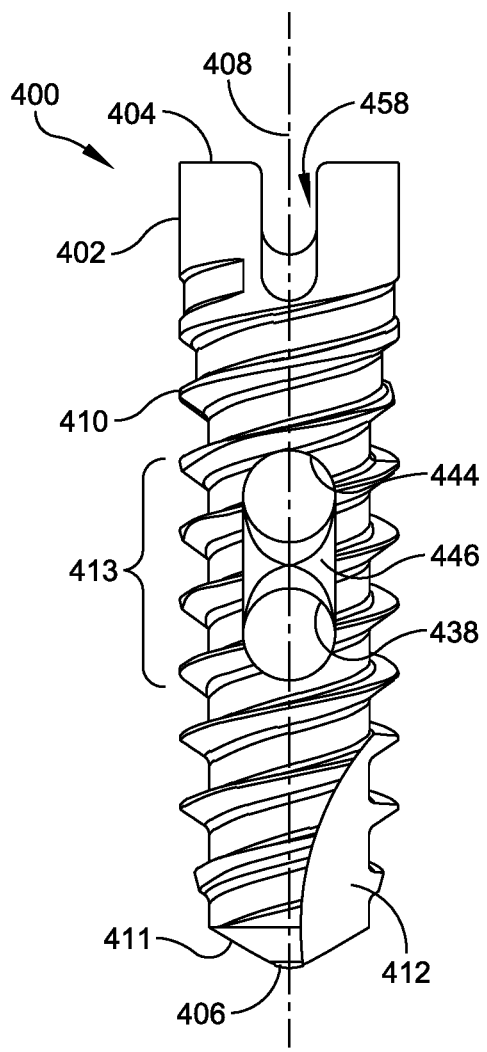
Figure 7:
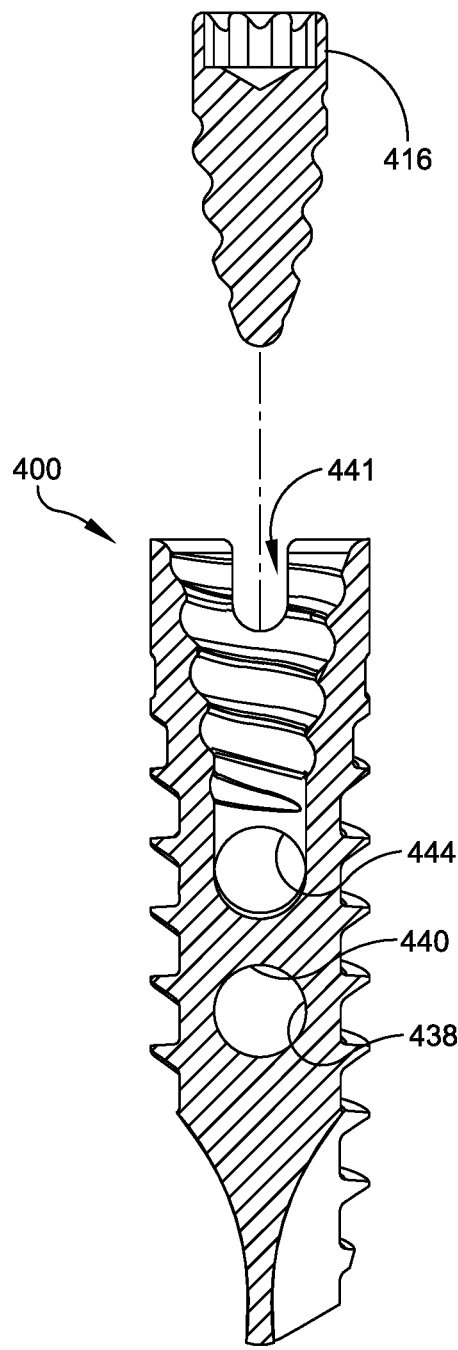

FIGS. 5-7 illustrate top, front, and cross-sectional exploded views of one embodiment of a suture returning and locking anchor 400. In FIGS. 5-7, the anchor 400 includes an anchor body 402 having a proximal end 404, a distal end 406, and defining a longitudinal axis 408. An external bone thread 410 extends around most of the body 402 except proximally where the thread runs out distal to the proximal end, and distally where the thread runs out at a tapered tip 411. The bone thread 410 includes a self-tapping flute 412 at the distal end. A set screw 416 is configured for rotational insertion and locking within the proximal end 404, as detailed further in relation to FIGS. 8-11 below.

The anchor 400 includes a suture return feature 413. In more detail and in this embodiment, the body 402 includes a first transverse hole 438 forming opposed openings on opposite sides of the body 402 through which a suture may be threaded to provide a suture return. While the external bone thread 410 is engaged in a bone, a flexible synthetic strand such as, for example, a suture, a suture tape, a cable or another suitable flexible synthetic strand (hereinafter a "flexible strand," "flexible synthetic strand," or "suture") may be pulled against a proximal margin 440 of the hole 438 to allow the suture to be tensioned. The body further includes an axial hole or passage 441 extending from an opening at the proximal end 404 toward the distal end 406. A second transverse hole 444 extends through the body 402 to form opposed openings on opposite sides of the body 402. The second transverse hole 444 is offset proximally from the first transverse hole 438 and communicates with the axial hole 441.

In use, a suture may be threaded into the axial hole 441 from the proximal end 404, out one of the openings of the second transverse hole 444, through the first transverse hole 438, in the other of the openings of the second transverse hole 444, and out the axial hole 441 so that the suture is routed about the proximal margin 440 within the proximal portion of the body 402.

The anchor body 402 may further contain relief grooves 446 connecting the openings of the first and second transverse holes 438, 444 on each side of the body 402. The relief grooves 446 allow the suture to pass from the axial hole 441 to the first transverse hole 438 while projecting less, or not at all, from the sides of the body 402 to protect the suture from abrasion and to allow the suture to slide more easily while it is being routed and tensioned. In this embodiment, the body 402 provides a tubular extension into a bone to protect the suture from abrasion from the bone as well as to protect the bone from abrasion or cutting from the suture.

The anchor 400 also includes a suture locking feature detailed in the example of FIGS. 8-11. FIG. 8 provides an enlarged view of the internal features of a proximal portion 403 of the body 402, and FIG. 9 provides a cross-sectional view of the proximal portion 403 of the body 402 in receipt of the set screw 416. In this embodiment, the proximal portion 403 of the body 402 includes a receiver 430 having a tapered receiver thread 432, and the set screw 416 has a tapered external thread 434. Both the receiver thread 432 and the set screw thread 434 are rounded knuckle threads. In addition, the receiver 430/receiver thread 432 and the set screw 416/set screw thread 434 feature multiple discrete taper angles that transition proximally to distally to provide for progressive gripping and releasing of the suture 418 to provide a strong grip on the suture while reducing the risk of suture damage or severing.

To address the taper angles in greater detail, FIGS. 10-11 illustrate the set screw 416 and the receiver 430 without their knuckle threading to better illustrate the gradual transitions of their tapers. In this embodiment, the set screw 416 is cylindrical at a proximal portion 450, has a relatively small angled taper over its mid portion 452, and has a relatively large angled taper over its distal portion 454 which terminates in a rounded tip 464. The receiver 430 has a relatively large angled taper at a proximal portion 456, has a relatively small angled taper over its mid portion 458, and is cylindrical at its distal portion 460. When the set screw 416 and the receiver 430 are mated, they provide progressively less clearance between them from the proximal end of the anchor 400 to their mid portions and progressively more clearance between them from their mid portions distally to the end of the set screw 416.

This opposing tapered configuration of the set screw 416 versus the receiver 430 incorporates the principal of the Morse taper for mating components. That is, the opposing conical shapes of the set screw 416 and the receiver 430 are closely matched in angle at their mid portions 452, 458, causing the respective surfaces of the set screw 416 and the receiver 430 to achieve an interference fit about the suture 418 over the mid portions 452, 458 of the set screw 416 and the receiver 430, with gradual transitions proximally leading into and distally leading out of the interference fit. This gradual transition of compression forces applied to the suture 418 disposed between the set screw 416 and the receiver 430 leads to an enhancement in suture fixation/locking strength, and simultaneously reduces the risk of severing the suture 418 that is present with greater magnitudes of compression force transition.

In one embodiment, the mid portions 452, 458 of the set screw 416 and the receiver 430 are of the same length and aligned. In this embodiment, there are three zones or amounts of clearance between the set screw 416 and the receiver 430 progressing in three steps from a relatively large amount of clearance proximally to a relatively small amount of clearance over their mid portions to a relatively large amount of clearance distally.

Alternatively, and as shown in the example of FIGS. 8-11, the set screw 416 can be driven so that the beginning of its mid portion 452 is positioned distal of the beginning of the receiver mid portion 458, and the end of the set screw mid portion 452 is positioned proximal of the end of the receiver mid portion 458, as shown in FIG. 11. This arrangement results in five clearance zones 440, 442, 444, 446, and 448 for an even more gradual progression of gripping and releasing of the suture 418. Any number of taper angle steps may be provided on the set screw 416 and the receiver 430, and any arrangement of overlap or radius blending may be provided to produce any number of progressive clearance steps to transition proximally to distally from no grip to maximum grip to no grip on the suture 418, protecting the suture through the gradual increase and decrease of stress placed on the suture 418.

Referring to FIG. 11, the first zone 440 provides the most clearance proximally and the clearance decreases distally at the angular difference between the cylindrical proximal portion 450 of the set screw 416 and the relatively larger angle of the proximal portion 456 of the receiver 430. The second zone 442 clearance decreases distally at the angular difference between the cylindrical proximal portion 450 of the set screw 416 and the relatively smaller angle of the mid portion 458 of the receiver 430. The third zone 444 provides the least clearance and corresponds to where the mid portions 452, 458 of the set screw 416 and the receiver 430 coincide. The fourth zone 446 clearance increases distally at the angular difference between the relatively smaller angle of the mid portion 458 of the receiver 430 and the relatively larger angle of the distal portion 454 of the set screw 316. The fifth zone 348 provides the most clearance distally and the clearance increases distally at the angular difference between the relatively larger angle of the distal portion 454 of the set screw 316 and the cylindrical portion 460 of the receiver 330.

In the illustrative example of FIGS. 8-11, the set screw 416 taper is cylindrical in the first proximal portion 450, 10 degrees per side in the second mid portion 452, and 20 degrees per side in the distal portion 454. The receiver 430 taper is 40 degrees per side in the first proximal portion 456, 10 degrees per side in a second mid portion 458, and cylindrical at a third distal portion 460. The resulting relief tapers corresponding to the five zones 440, 442, 444, 446, 448 illustrated in FIG. 11, proximally to distally, are 20 degrees, 10 degrees, 0 degrees, 10 degrees, and 20 degrees. In this embodiment, the proximal ends 461, 463 of the receiver 430 and the set screw 416 are chamfered and the distal end 464 of the set screw 416 is rounded to further eliminate any sharp edges to further smooth the path of the suture and to provide easier starting of the screw.

While the embodiment of the suture locking feature of FIGS. 8-11 features opposing tapers on the set screw 416 and the receiver 430, it should be understood that the invention contemplates any appropriate tapering configuration that provides a gradual increase and decrease of compression forces applied, proximally to distally, to the interference fit of the suture 418 between the set screw 416 and the receiver 430. For example, the set screw 416 may be entirely cylindrical through its proximal, mid, and distal portions, maintaining the above described configuration of the receiver 430. In another example, the proximal, mid, and distal portions 450, 452, 454 of the set screw 416 may be angled to form an egg-like or football shape, while the proximal, mid, and distal portions 456, 458, 460 of the receiver 430 remain cylindrical.

The locking feature discussed in relation to FIGS. 8-11 provides both a knotless and reversible mechanism for locking out the suture 418 relative to the returning and locking anchor 400. Because an interference fit between the suture 418, the set screw 416, and the receiver 430 provides the compression force required to secure the suture 418 in tension relative to the anchor 400, the locking feature provides a knotless fixation, thereby reducing the probability of bone and/or tissue abrasion and/or aggravation that is often caused by knotted fixations. Moreover, because the locking mechanism protects the integrity of the suture through the gradual increase and decrease of stress placed on the suture 418, discussed above, the knotless fixation is truly reversible in that the set screw 416 may be rotationally inserted to lock out the suture 418 relative to the anchor 400 without damaging the suture 418 and/or risking its structural integrity. As a result, a surgeon may lock and unlock the suture 418 relative to the anchor 400 multiple times to achieve an optimal fixation while maintaining confidence in the quality of the ultimate knotless fixation.

The body 402 of the suture returning and locking anchor 400 further includes a driver feature 458 in the form of opposing slots 462 (FIG. 16) formed in the proximal wall of the body 402 for receiving an anchor driver such that the anchor driver does not block the receiver 430 from receiving the set screw 416 and for providing counter-torque stabilization such that a set screw driver does not axially shift the body 402 during insertion of the set screw 416, as discussed further below in relation to 15-18.

Figures 12, 13, 14:
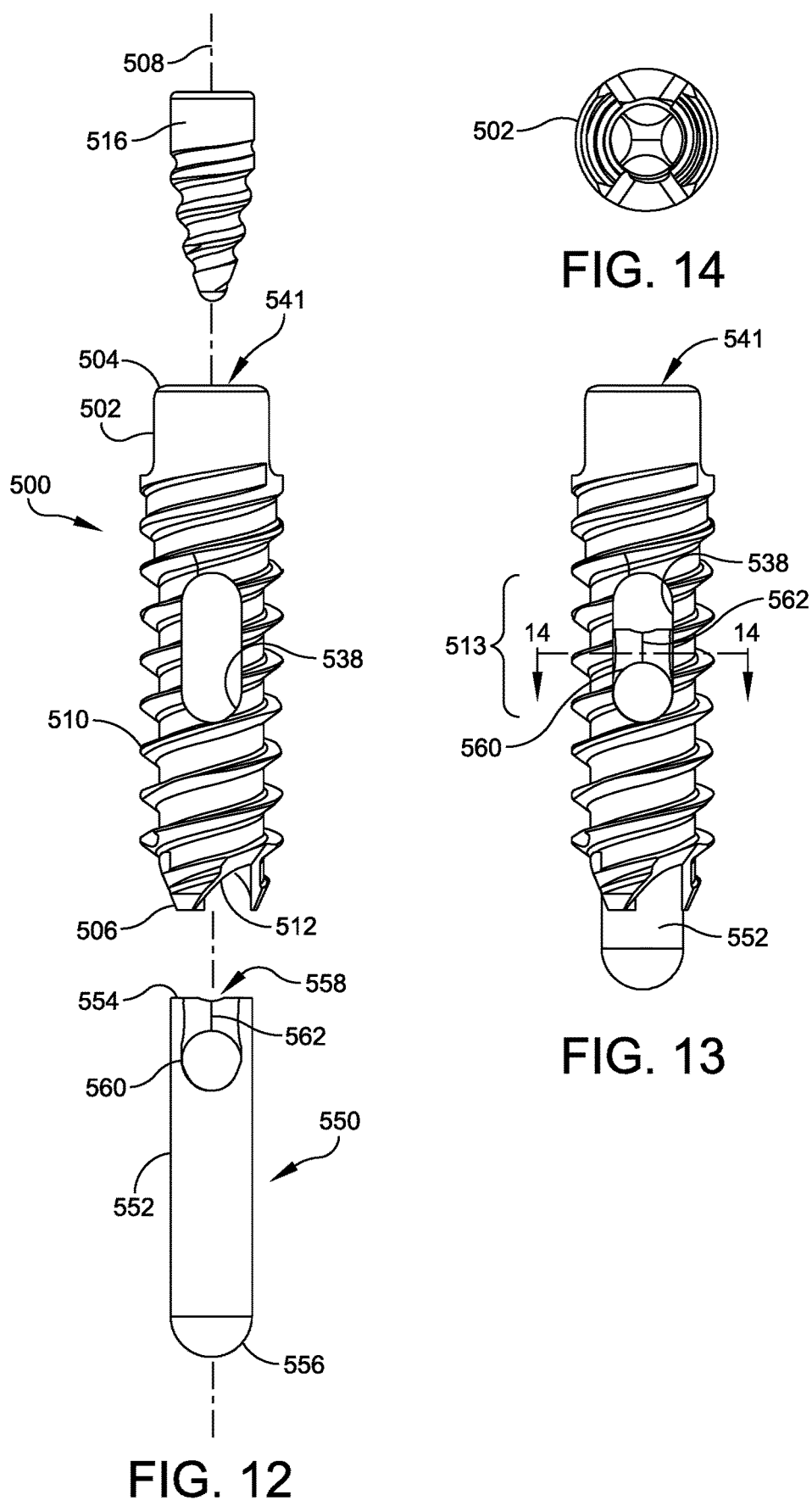
FIGS. 12-14 illustrate respective exploded, front, and cross-sectional views of another embodiment of a suture returning and locking anchor.

FIGS. 12-14 illustrate exploded, front, and cross-sectional views of another example of a suture returning and locking anchor 500 that is similar to the anchor 400. However, the anchor 500 of FIGS. 12-14 is a two-piece anchor having an axial through-hole 541 that extends through an entirety of a body 502 of the anchor 500.

In this embodiment, the anchor 500 includes the anchor body 502 having a proximal end 504, a distal end 506, and defining a longitudinal axis 508. An external bone thread 510 extends around most of the body 502 except proximally where the thread runs out. The bone thread 510 includes a self-tapping flute 512 at the distal end. A set screw 516 is configured for rotational insertion and locking according to the locking arrangement discussed above in relation to FIGS. 8-11.

The anchor 500 may provide a suture return function either internally or externally. In an internal configuration, the anchor 500 may incorporate a removable suture return insert 550. The suture return insert 550 includes a longitudinal body 552 centered about the longitudinal axis 508 and sized to press fit within the axial hole 541 extending through the anchor body 502. The suture return insert 550 has a proximal end 554, a closed distal end 556, and an axial hole or passage 558 extending distally from the proximal end 554. A first transverse hole 560 forms opposed openings on opposite sides of the insert body 552. The first transverse hole 560 communicates with the axial hole 558 of the insert body 552 such that when the proximal end 554 of the insert 500 is inserted into the distal end 506 of the anchor body 502, the first transverse hole 560 within the insert body 552 aligns with a distal portion of a second transverse hole 538 within the anchor body 502 to form an internal suture return feature 513, as shown in FIG. 13, which is similar to the return feature 413 discussed above in relation to the anchor 400 of FIGS. 5-7.

In use in the internal configuration, a suture may be threaded into the axial hole 541 of the anchor 500 from the proximal end, out one of the openings of the second transverse hole 538 in the anchor body 502, through the first transverse hole 560 in the insert 550, in the other of the openings of the second transverse hole 538, and out the communicating axial holes 441, 558 of the anchor body 402 and the insert body 552 such that the suture is routed within the proximal portion of the anchor 500. The insert body 552 may further contain relief grooves 562 connecting the openings of the first and second transverse holes 560, 538 on each side of the anchor 500, when the insert 550 is disposed within the anchor body 502. The relief grooves 562 allow the suture to pass from the axial holes 541, 558 to the first transverse hole 560 while projecting less, or not at all, from the sides of the anchor body 502 to protect the suture from abrasion and to allow the suture to slide more easily while it is being routed and tensioned.

In an external configuration, the return insert 550 is excluded and the suture return is formed by either the second transverse hole 538 or the distal end 506 of the anchor body 502. In use in the external return configuration, the suture enters the axial hole 541 at the proximal end 504 of the anchor 500 and exits the axial hole 541 at either the second transverse hole 538 or the distal end of the anchor 500, with a return suture path outside the anchor body 502. In various embodiments, the return suture path passes through a notch or recess formed in the outer wall of the anchor body, through a relief groove in the bone that projects radially from the bone tunnel, as formed by, for example, the noncircular punch and associated methods disclosed in FIGS. 2-10 of U.S. patent application Ser. No. 15/641,600, entitled "NONCIRCULAR BROACH AND METHODS OF USE" and co-filed with this application on Jul. 5, 2017, or in any other appropriate return path or routing manner. Alternatively, the suture may exit the distal end 506 of the anchor and continue on a path directly to another fixation point (e.g., continue along the longitudinal axis 508, without a return, within a bone tunnel to another locking anchor).

Counter-Torque Anchor Driver

FIGS. 15-18 illustrate an example of an anchor driver 570 for use with, for example, the anchor 400 of FIGS. 5-7. The anchor driver includes an elongated body 572 extending from a proximal end 574 to a distal end 576 and defining a longitudinal axis 578. The distal end 576 of the driver includes opposed clearance slots 580, 582 opening distally and defining spaced apart driver legs 584, 586. The distal ends of the driver legs 584, 586 form opposing tabs 588 that engage the opposed slots 462 of the anchor 400. The driver tabs 588 and driver slots 580, 582 are sized so that with the tabs 588 fully engaged in the slots 462 of the anchor, the driver slots 580, 582 provide clearance 592, 594 between the driver 570 and the anchor 400 for the suture 418.

A portion of each tab 588 abuts the proximal end of the anchor 400 and provides a distal facing bearing surface to resist forces (e.g., torsional forces) generated when tensioning the suture 418 via a rotational input from a set screw driver (not shown) to the set screw 416 to engage the locking mechanism discussed above in relation to FIGS. 8-11. The anchor driver 570 includes an axial through hole 596 to allow passage of the set screw 416 and the set screw driver (not shown) for locking the suture 418.

In use, for example, the anchor 400 is driven into a bone by engaging the tabs 588 of the anchor driver 570 with the slots 462 in the anchor, as shown in FIG. 18, and rotating the anchor driver 570. A suture 418 is threaded through the anchor 400 and passed through the clearance 592, 594 outside of the driver 570, if the anchor driver 570 has not already been removed. The suture is tensioned and then the set screw 416 is driven into the anchor 400 to lock the suture. If the anchor driver 570 is still engaged with the anchor 400, the set screw 416 may be inserted through the axial through hole 596 in the anchor driver 570. The torsional force resistance provided by the anchor driver 570 engagement with the slots 462 ensures that forces applied in locking the suture via the set screw 416 do not affect or alter the original insertion alignment of the anchor 400.

Constructs and Operative Sequences

FIGS. 19-26 illustrate a number of examples of embodiments of the disclosed devices in use to stabilize or reinforce ligaments and/or bone fractures. In the example of FIGS. 19-22, the exemplary devices and methods are shown in use in a stabilization construct reinforcing the pubic symphysis 2114 to stabilize the pelvis 2100 after an anterior-posterior compression fracture 2116.

Referring to FIGS. 19 and 20, a first anchor 2120 is inserted into the pubis 2110 of a first hip bone 2104 from superior to inferior. A flexible strand 2122 is connected to the first anchor 2120 and extends from the trailing end of the first anchor. In the embodiments disclosed herein, the flexible strand may be a suture, a suture tape, a cable or another suitable synthetic flexible strand. In the example of FIGS. 19-22, the flexible strand 2122 is a braided high strength suture tape.

A second anchor 2124 such as, for example, anchors 400 or 500 discussed above in relation to FIGS. 5-13, is inserted into the pubis 2111 of a second hip bone 2105 from superior to inferior. The position of the second anchor 2124 is shown via the broken-out section view of FIG. 20, in which the second anchor 2124 is shown in cross section. A suture threader or passer 2126 extends into the proximal or trailing end of the second anchor 2124, around a return feature 2128, and out the proximal or trailing end of the second anchor 2124. The flexible strand 2122 is then threaded through a loop of the passer 2126.

Figure 21:
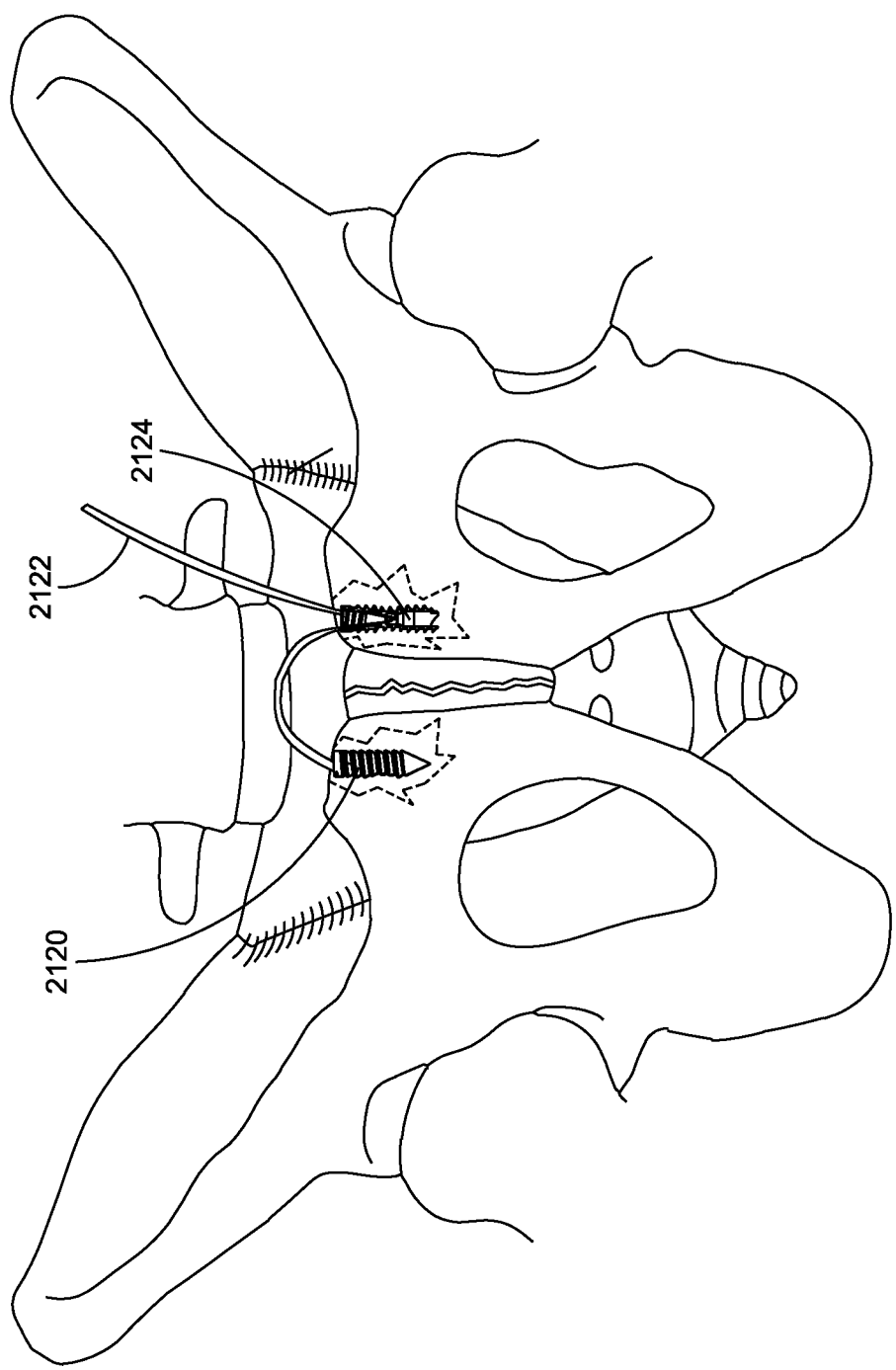
Figure 22:
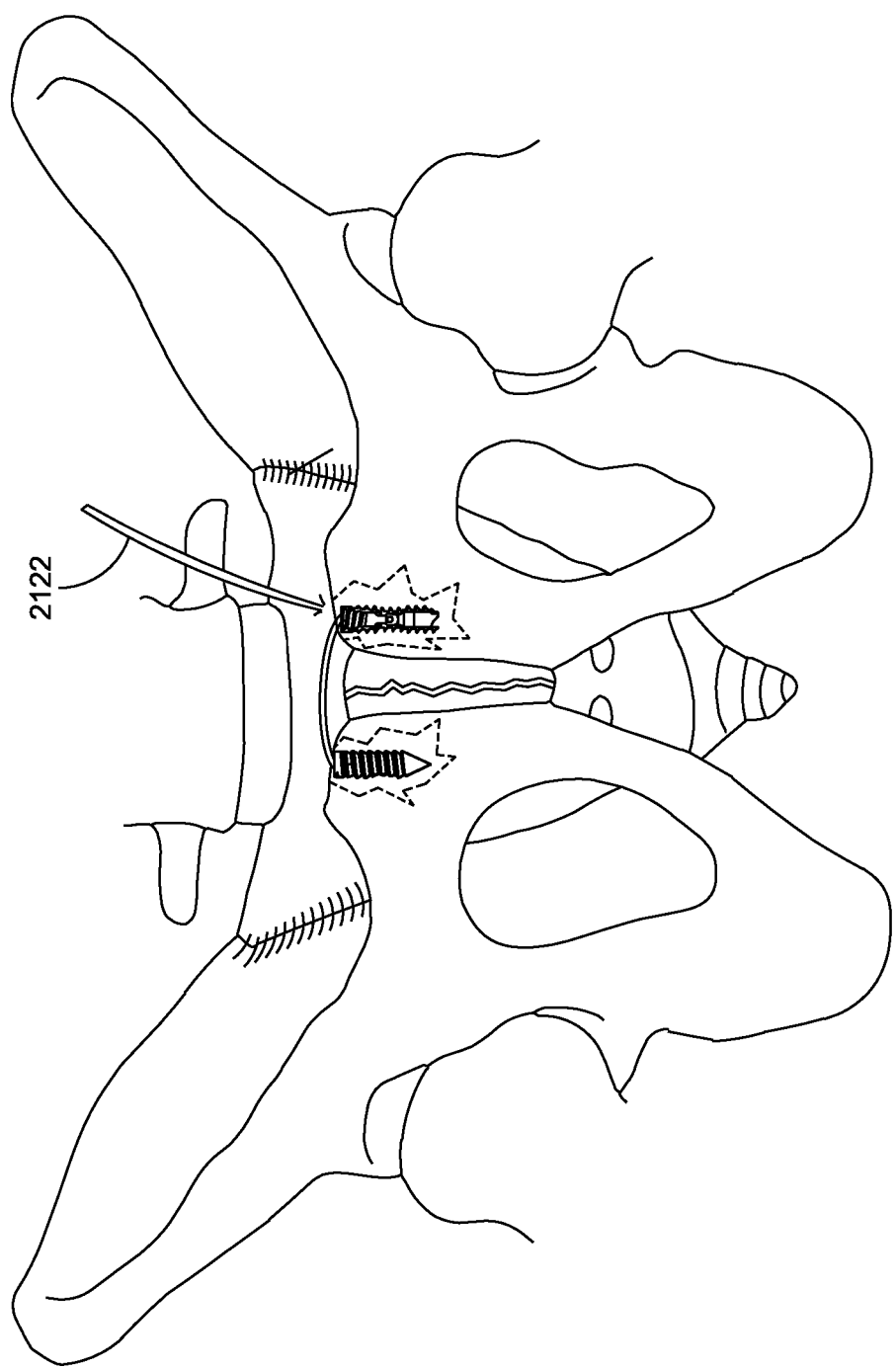

Referring to FIG. 21, the passer 2126 has been withdrawn from the proximal end of the second anchor 2124 to pass the end of the flexible strand 2122 into the trailing end or proximal end of the second anchor 2124, around the return feature 2128, and out the trailing end of the second anchor 2124. A tension instrument such as, for example, the tension instrument 700 disclosed in FIGS. 12-15 of U.S. patent application Ser. No. 15/642,053, entitled "COMPRESSION AND TENSION INSTRUMENTS AND METHODS OF USE TO REINFORCE LIGAMENTS" and co-filed with this application on Jul. 5, 2017, may then be used to pull the flexible strand 2122 to tension the portion of the flexible strand 2122 extending between the anchors 2120 and 2124 and reduce the pubic symphysis. The flexible strand 2122 may then be locked relative to the second anchor 2124 to maintain the reduction in any appropriate manner including, for example, employing the tension instrument 700 disclosed in FIGS. 12-15 of U.S. patent application Ser. No. 15/642,053, entitled "COMPRESSION AND TENSION INSTRUMENTS AND METHODS OF USE TO REINFORCE LIGAMENTS" and co-filed with this application on Jul. 5, 2017, employing the suture locking feature discussed above in relation to FIGS. 8-11, employing the anchor driver 570 discussed above in relation to 15-18, and/or employing a set screw driver as known in the art. In this regard, a set screw may be advanced through a central cannulation in the tension instrument before a set screw driver is advanced through the central cannulation in the tension instrument and used to thread the set screw into the internal threads formed in the second anchor 2124 to lock the flexible strand 2122 relative to the second anchor at the desired tension. The tension instrument may then be released and removed. Once the flexible strand is locked, the excess length of the flexible strand 2122 may be trimmed, as shown in FIG. 22.

A novel repair construct according to examples of the invention has been shown with anchors inserted into the superior portion of the pubis to create a superior tension band. However, it will be understood that the anchors may be inserted in other orientations and at other locations. For example, the anchors may be inserted in the superior portion of the pubis but directed anterior to posterior or at some angle between superior-inferior and anterior-posterior. Likewise, the anchors may be inserted inferior to the positions shown in the illustrative example of FIGS. 19-22 to create an anterior tension band midway between the superior and inferior aspects of the pubis. Multiple bands may be applied at various levels as needed to achieve stability. Reinforcement/repair of the sacroiliac joint may be combined with the anterior reinforcement.

Figure 1:
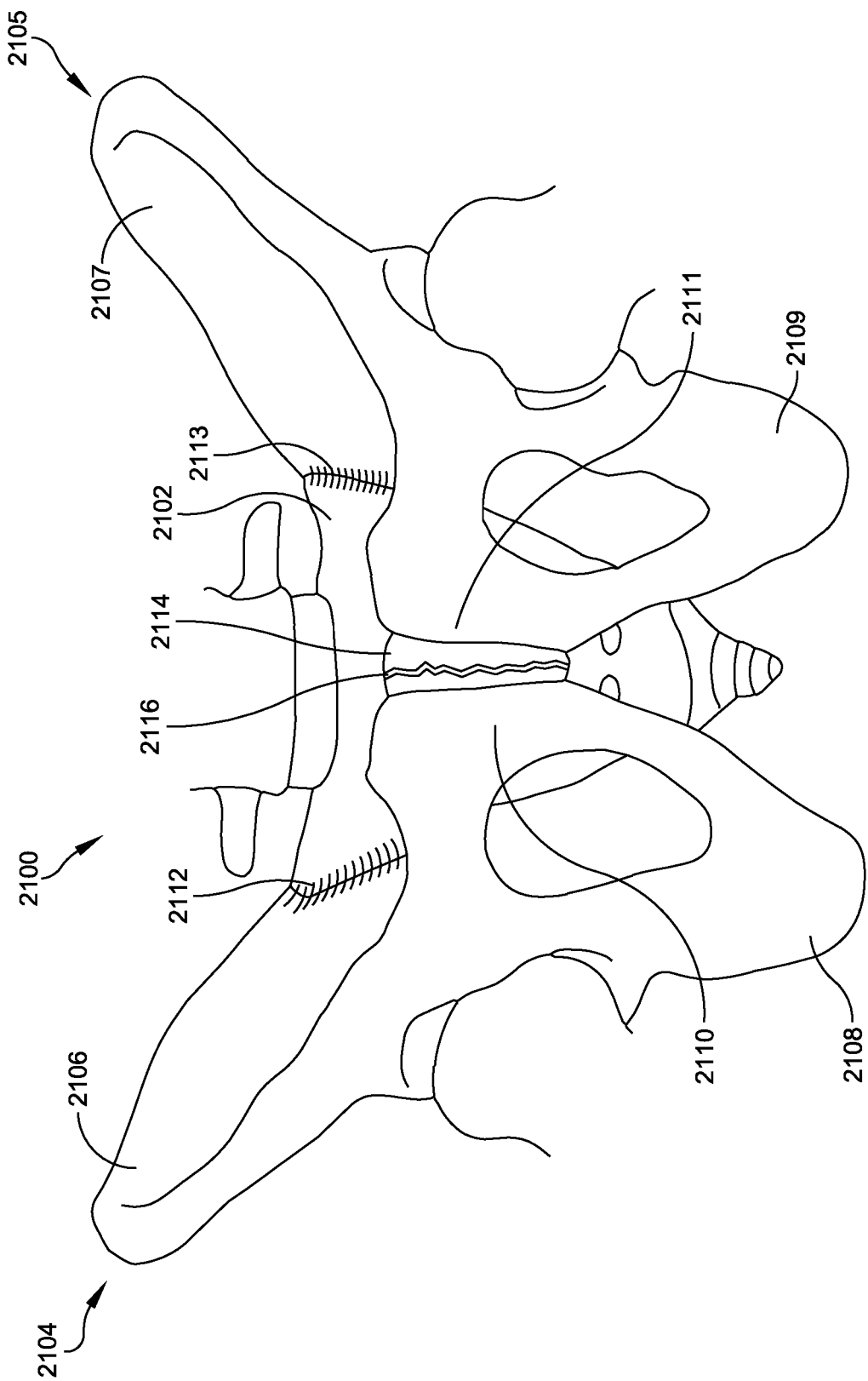
FIG. 1 illustrates an anterior view of a human pelvis having an anterior-posterior compression fracture.
Figure 2:
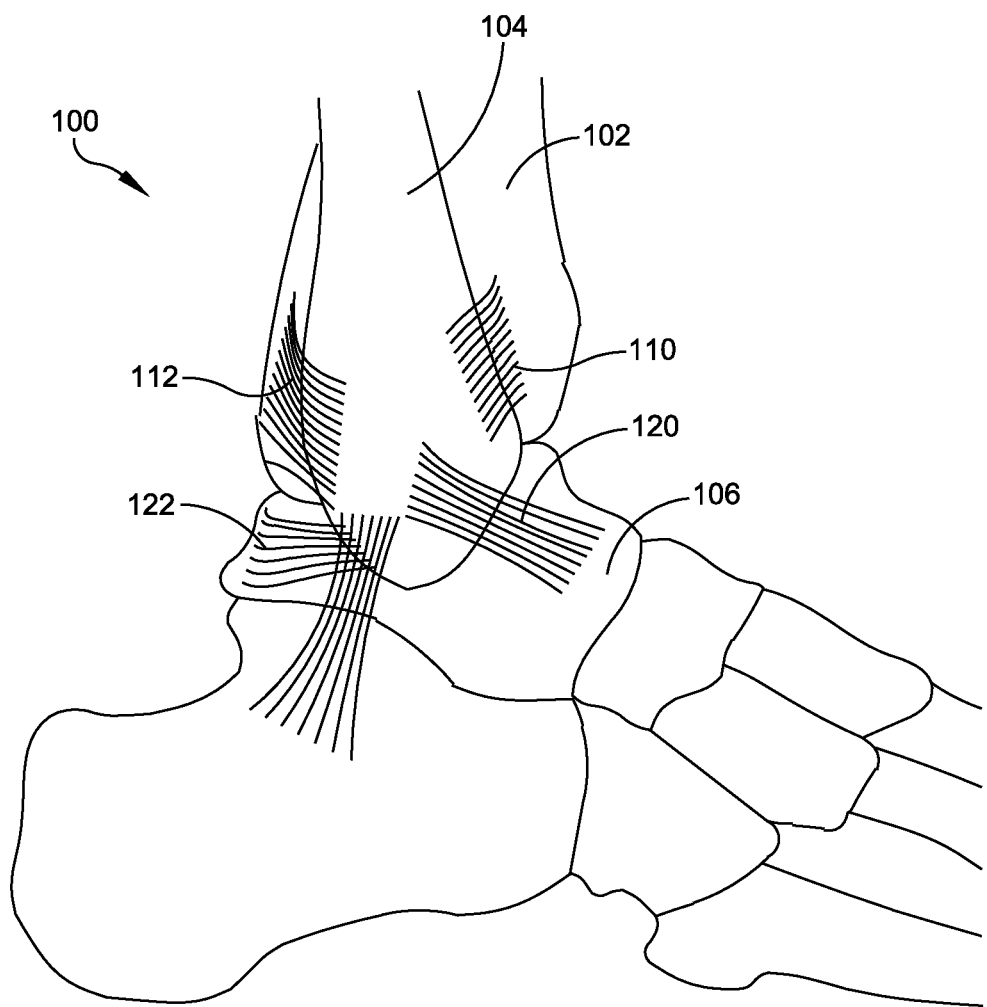
FIG. 2 illustrates a right view of a human ankle joint.
Figure 3:
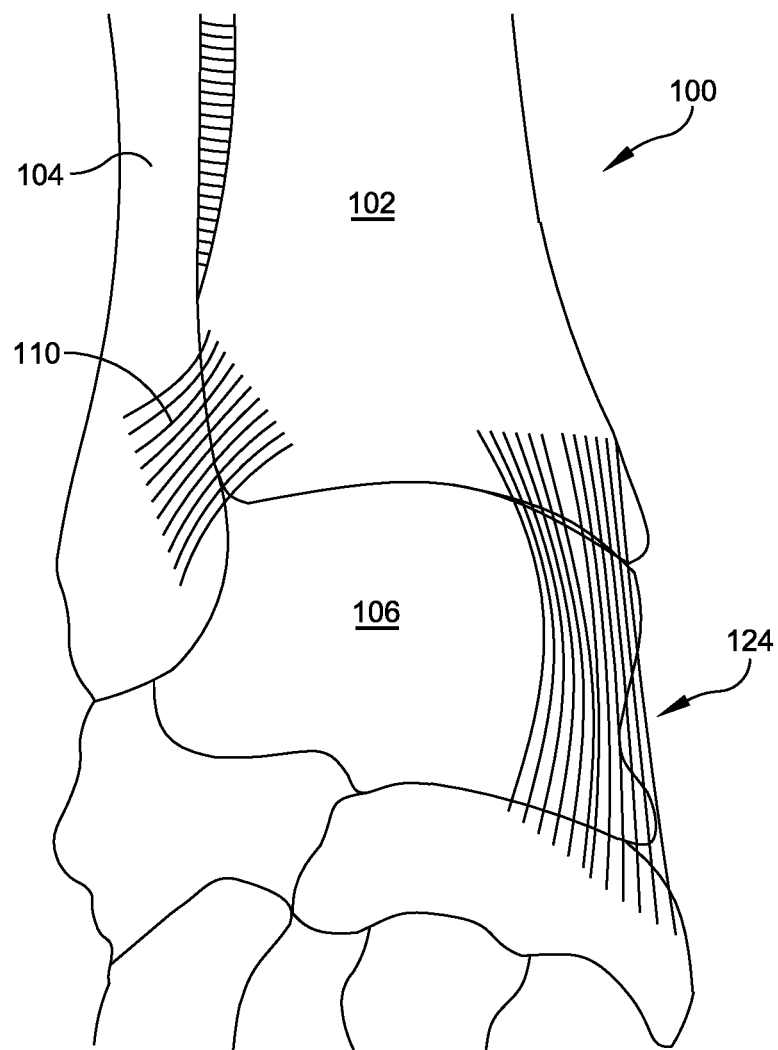
FIG. 3 illustrates a front view of a human ankle joint.
Figure 4:
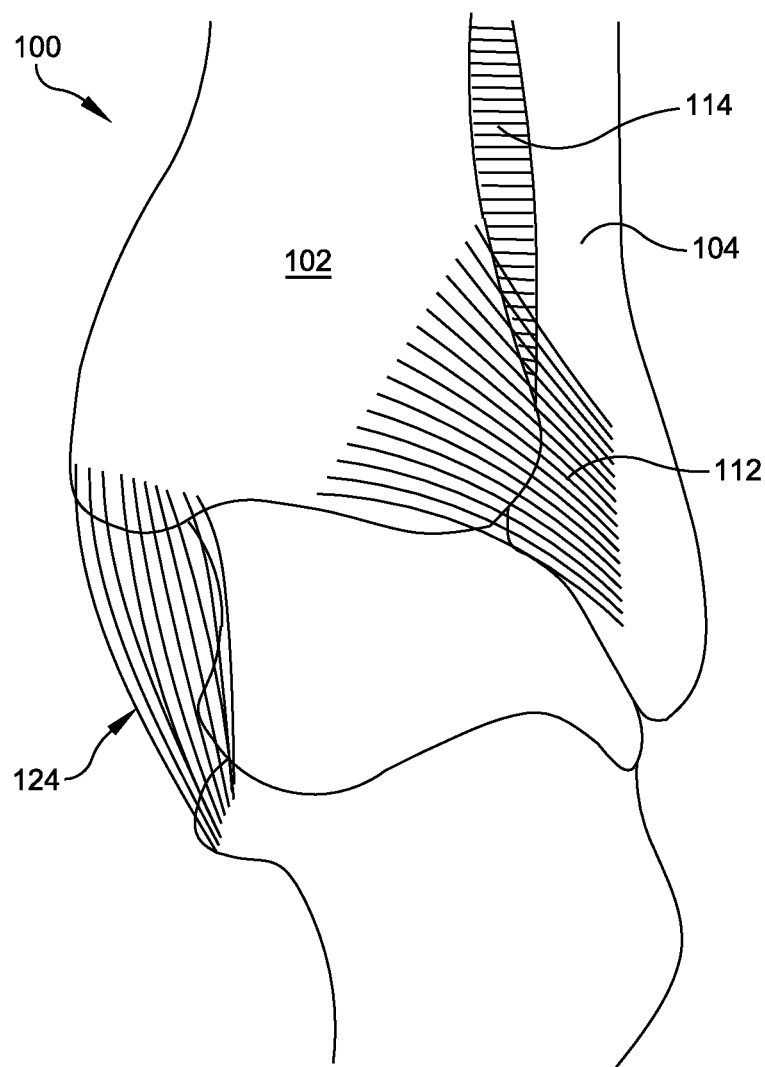
FIG. 4 illustrates a rear view of a human ankle joint.

While FIGS. 19-22 detail an exemplary method and associated devices for forming a fracture repair construct, similar methods and devices may be used to form ligament reinforcement constructs such as, for example, within the human ankle 100 detailed in FIGS. 2-4 above.

Figure 23:
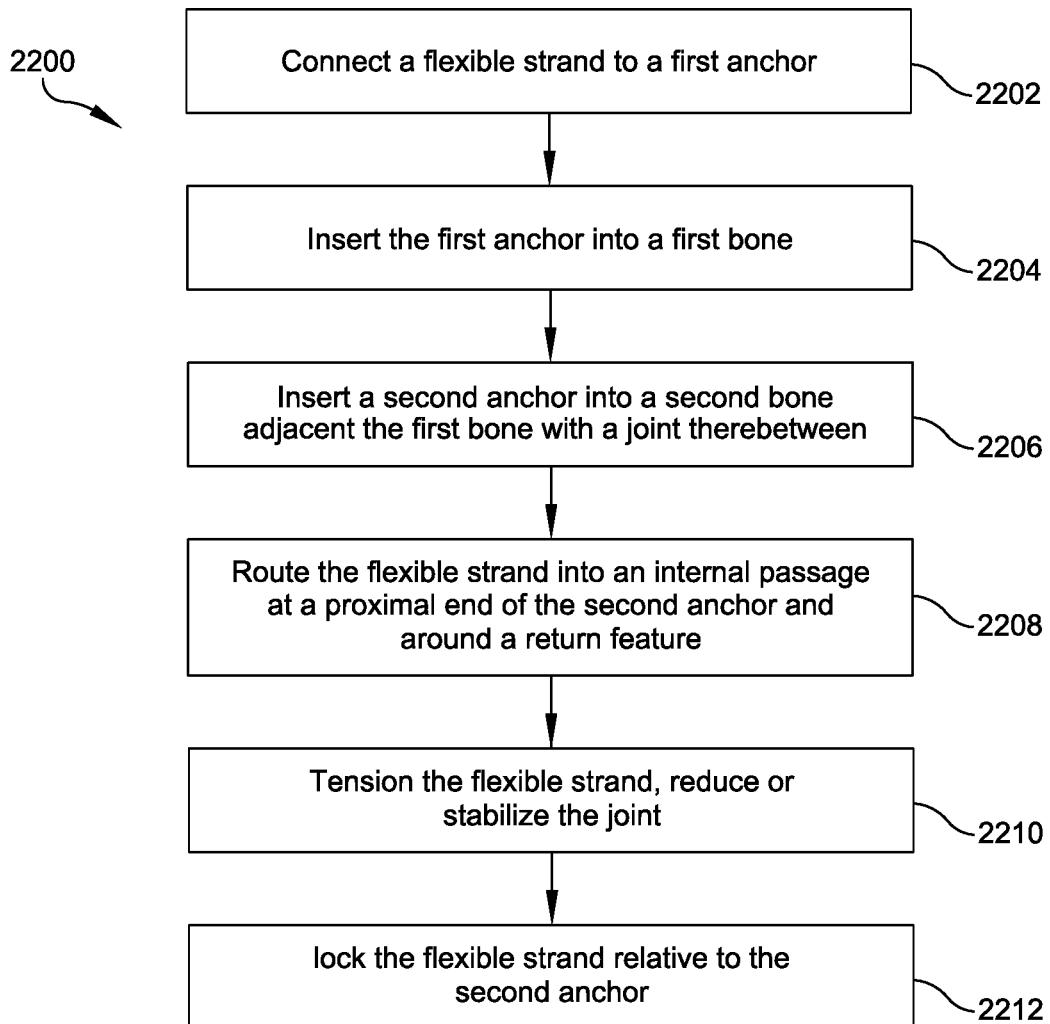
FIG. 23 provides a flowchart detailing the operative sequence illustrated by FIGS. 19-22.

In another exemplary method, and with reference to FIG. 23, there may be provided a method of at least one of reducing or stabilizing a joint. The method may include connecting 2202 a flexible strand to a first anchor. The method may include inserting 2204 the first anchor into a first bone. The method may include inserting 2206 a second anchor into a second bone adjacent the first bone with a joint there between. The method may include routing 2208 the flexible strand into an internal passage at the proximal end of the second anchor and around a return feature. The method may include tensioning 2210 the flexible strand to reduce or stabilize the joint. The method may include locking 2212 the suture to the flexible strand. In an embodiment, the routing of the flexible strand into the internal passage at the proximal end of the second anchor and around the return feature may include exiting the flexible strand from the internal passage out of the proximal end of the second anchor. In another embodiment, the routing of the flexible strand into the internal passage at the proximal end of the second anchor and around the return feature may include exiting the flexible strand from the internal passage out of a side aperture formed through the second anchor. In another embodiment, the routing of the flexible strand into the internal passage at the proximal end of the second anchor and around the return feature may include exiting the flexible strand from the internal passage out of a distal end of the second anchor. Locking the suture to the flexible strand may include a reversible configuration so as to further allow unlocking the flexible strand relative to the second anchor. Locking the suture to the flexible strand may include applying a screw.

Figure 24:
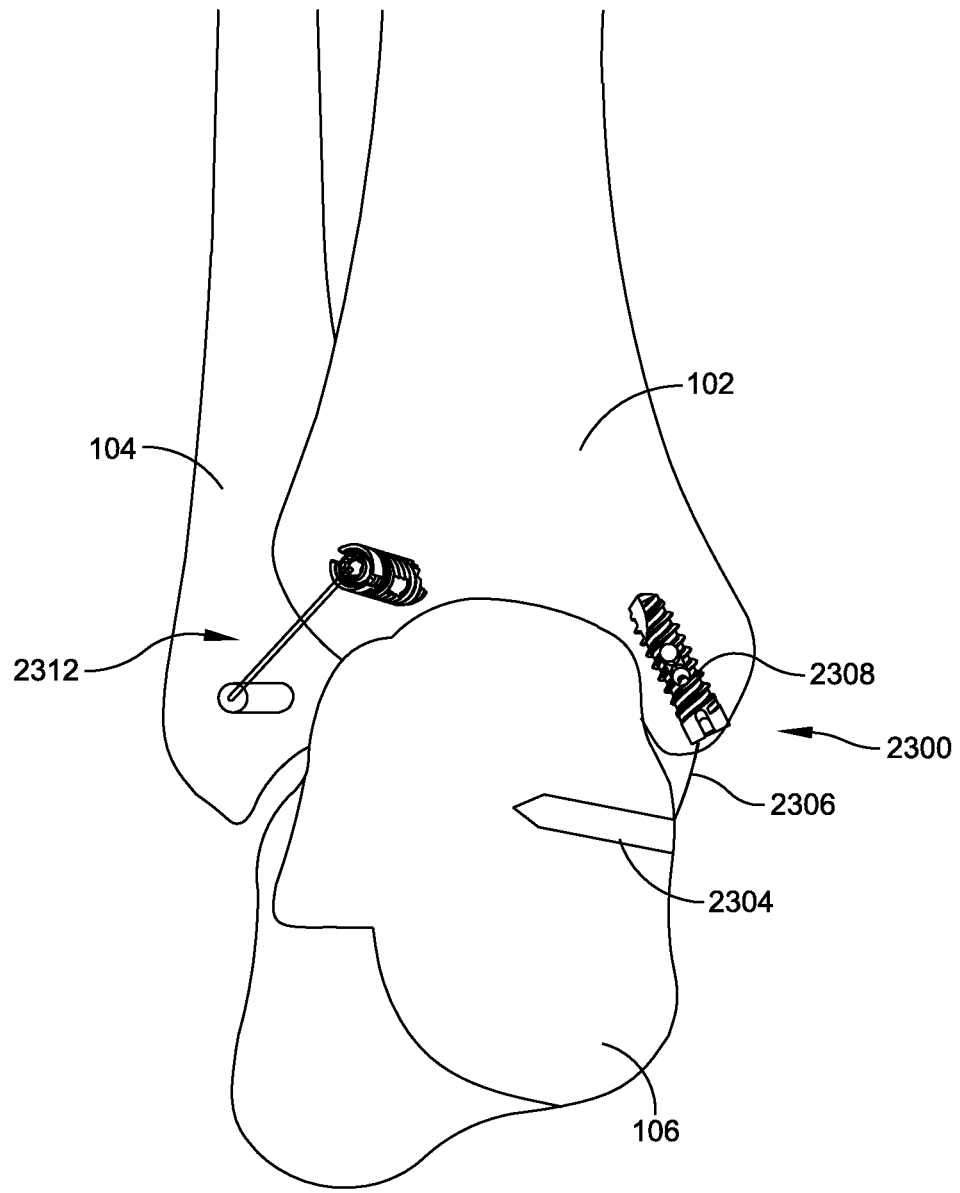
FIG. 24 illustrates exemplary reinforcement constructs for the deltoid ligament complex and the posterior inferior tibiofibular ligament (PITFL)/anterior inferior tibiofibular ligament (AITFL) according to embodiments of the disclosed devices.

FIG. 24 illustrates a first ligament reinforcement construct 2300 for reinforcing the deltoid ligament complex 124 (FIG. 3). In this construct embodiment, a suture anchor 2304 with a trailing suture 2306 has been placed in the talus 106. A second suture returning and locking anchor 2308 such as, for example, one of anchors 400 or 500 discussed above in relation to FIGS. 5-13 has been placed in the medial malleolus of the tibia 102. In this example, the suture 2306 trailing from the anchor 2304 is threaded through the second anchor 2308, tensioned, e.g., manually or using a tension instrument such as, for example, tension instrument 700 disclosed in FIGS. 12-15 of U.S. patent application Ser. No. 15/642,053, entitled "COMPRESSION AND TENSION INSTRUMENTS AND METHODS OF USE TO REINFORCE LIGAMENTS" and co-filed with this application on Jul. 5, 2017, and locked or affixed with a set screw as discussed above in relation to FIGS. 8-11. FIG. 24 also shows a separate and similar ligament reinforcement construct 2312 for reinforcement of, for example, the posterior inferior tibiofibular ligament (PITFL) 112 or the anterior inferior tibiofibular ligament (AITFL) 110 (FIGS. 2-4).

Figure 25:
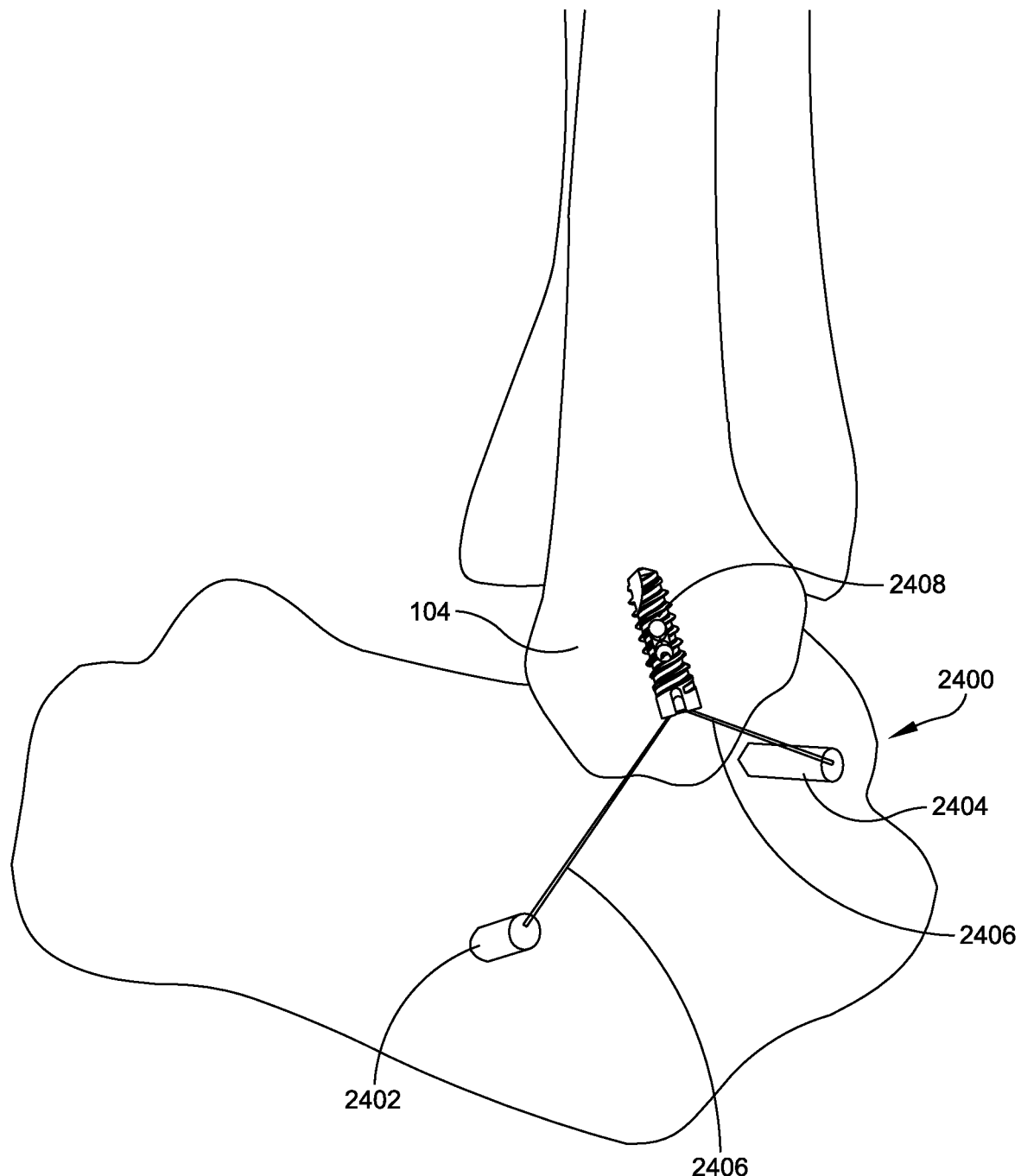
FIG. 25 illustrates one embodiment of a ligament reinforcement construct using a single suture returning and locking anchor to reinforce two separate ligaments according to embodiments of the disclosed devices.

FIG. 25 illustrates another reinforcement construct 2400 for reinforcing, for example, the anterior talofibular ligament (ATFL) 120, the posterior talofibular ligament (PTFL) 122, or other ligaments. In the example of FIG. 25, two suture anchors 2402, 2404 have been placed with suture 2406 to reinforce two separate ligaments, but a single suture returning and locking anchor 2408 such as, for example, the anchors 400 or 500 discussed above in relation to FIGS. 5-13, has been placed in the fibula 104 to secure both ligaments to a common attachment or fixation point.

Figure 26:
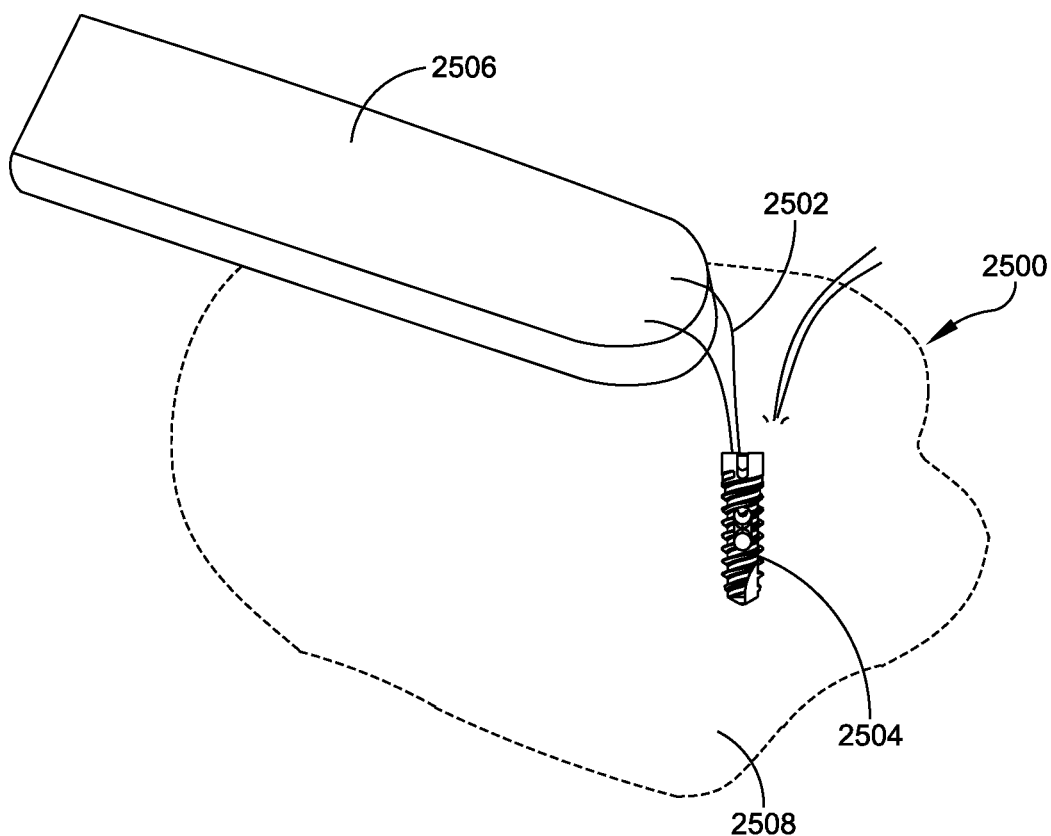
FIG. 26 illustrates one embodiment of an attachment construct for soft tissue repair or tendon reattachment according to embodiments of the disclosed devices.

Beyond the reinforcement and repair constructs discussed above, suture ends from embodiments of the returning and locking anchors discussed above may be used to attach other soft human or allograft tissues. FIG. 26 illustrates an exemplary attachment construct 2500 in which a suture returning and locking anchor 2504 such as, for example, one of the anchors 400 or 500 discussed above in relation to FIGS. 5-13 has been employed for the purpose of soft tissue repair or tendon reattachment. In this embodiment, a flexible strand such as a suture 2502 is passed through a tendon 2506 (e.g., Achilles tendon, rotator cuff tendon, etc.), allograft, or other soft tissue before being threaded through the anchor 2500, which is affixed with an appropriate bone 2508, tensioned, and locked, as discussed above.

Notably, any combination of ordinary suture anchors, suture returning anchors, suture locking anchors, suture returning and locking anchors, and any number of sutures per anchor may be combined to produce a variety of constructs with one-to-one or many-to-one relationships.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A method of at least one of reducing and stabilizing a joint, the method comprising:
   inserting a first anchor into a first bone;
   inserting a second anchor into a second bone adjacent the first bone with a joint there between;
   routing a flexible strand connected to the first anchor into an internal passage at the proximal end of the second anchor and around a return feature;
   tensioning the flexible strand to reduce or stabilize the joint; and
   moving a locking member within the second anchor to lock the flexible strand to the second anchor.

2. The method of claim 1, wherein the routing the flexible strand into the internal passage at the proximal end of the second anchor and around the return feature includes exiting the flexible strand from the internal passage out of the proximal end of the second anchor.

3. The method of claim 1, wherein the routing the flexible strand into the internal passage at the proximal end of the second anchor and around the return feature includes exiting the flexible strand from the internal passage out of a side aperture formed through the second anchor.

4. The method of claim 1, wherein the routing the flexible strand into the internal passage at the proximal end of the second anchor and around the return feature includes exiting the flexible strand from the internal passage out of a distal end of the second anchor.

5. The method of claim 1, wherein the locking the suture to the flexible strand includes a reversible configuration so as to further allow unlocking the flexible strand relative to the second anchor.

6. The method of claim 1, wherein the locking the suture to the flexible strand includes applying a screw.

7. The method of claim 1, wherein the locking member locks the flexible strand to the second anchor by pressing the flexible strand against the internal passage.

8. The method of claim 1, wherein the return feature is formed as a single piece with the proximal end.

9. A method of at least one of reducing and stabilizing a joint, the method comprising:
   inserting a first anchor into a first bone;
   inserting a second anchor into a second bone adjacent the first bone with a joint there between;
   routing a flexible strand connected to the first anchor into an internal passage at the proximal end of the second anchor and around a return feature;
   tensioning the flexible strand to reduce or stabilize the joint; and
   locking the flexible strand to the second anchor by pressing the flexible strand against the internal passage.

10. The method of claim 9, wherein the routing the flexible strand into the internal passage at the proximal end of the second anchor and around the return feature includes exiting the flexible strand from the internal passage out of the proximal end of the second anchor.

11. The method of claim 9, wherein the routing the flexible strand into the internal passage at the proximal end of the second anchor and around the return feature includes exiting the flexible strand from the internal passage out of a side aperture formed through the second anchor.

12. The method of claim 9, wherein the routing the flexible strand into the internal passage at the proximal end of the second anchor and around the return feature includes exiting the flexible strand from the internal passage out of a distal end of the second anchor.

13. The method of claim 9, wherein the locking the suture to the flexible strand includes a reversible configuration so as to further allow unlocking the flexible strand relative to the second anchor.

14. The method of claim 9, wherein the locking the suture to the flexible strand includes applying a screw.

15. A method of at least one of reducing and stabilizing a joint, the method comprising:
- inserting a first anchor into a first bone;
- inserting a second anchor into a second bone adjacent the first bone with a joint there between;
- routing a flexible strand connected to the first anchor into an internal passage at the proximal end of the second anchor and around a return feature formed as a single piece with the proximal end;
- tensioning the flexible strand to reduce or stabilize the joint; and
- locking the flexible strand to the second anchor.

16. The method of claim 15, wherein the routing the flexible strand into the internal passage at the proximal end of the second anchor and around the return feature includes exiting the flexible strand from the internal passage out of the proximal end of the second anchor.

17. The method of claim 15, wherein routing the flexible strand into the internal passage at the proximal end of the second anchor and around the return feature includes exiting the flexible strand from the internal passage out of a side aperture formed through the second anchor.

18. The method of claim 15, wherein the routing the flexible strand into the internal passage at the proximal end of the second anchor and around the return feature includes exiting the flexible strand from the internal passage out of a distal end of the second anchor.

19. The method of claim 15, wherein the locking the suture to the flexible strand includes a reversible configuration so as to further allow unlocking the flexible strand relative to the second anchor.

20. The method of claim 15, wherein the locking the suture to the flexible strand includes applying a screw.

* * * * *